United States Patent [19]
Augustine

[11] Patent Number: 6,095,992
[45] Date of Patent: *Aug. 1, 2000

[54] WOUND TREATMENT APPARATUS FOR NORMOTHERMIC TREATMENT OF WOUNDS

[75] Inventor: Scott D. Augustine, Bloomington, Minn.

[73] Assignee: Augustine Medical, Inc., Eden Prairie, Minn.

[ * ] Notice: This patent is subject to a terminal disclaimer.

[21] Appl. No.: 09/055,605

[22] Filed: Apr. 6, 1998

[51] Int. Cl.$^7$ ........................................... A61F 7/00
[52] U.S. Cl. ................................ 602/2; 602/14; 604/113; 607/96; 607/108; 607/114
[58] Field of Search ..................... 602/2, 14, 42, 602/43, 54, 57; 604/113, 114; 607/96, 108–112, 114

[56] References Cited

U.S. PATENT DOCUMENTS

| | | | |
|---|---|---|---|
| 3,867,939 | 2/1975 | Moore | 607/96 |
| 5,190,031 | 3/1993 | Guibert et al. | 607/96 |
| 5,662,624 | 9/1997 | Sundstrom et al. | 602/2 |
| 5,817,145 | 10/1998 | Augustine et al. | 602/2 |
| 5,871,526 | 2/1999 | Gibbs et al. | 607/114 |
| 5,947,914 | 9/1999 | Augstine | 602/2 |
| 5,954,680 | 9/1999 | Augustine | 602/2 |
| 5,964,721 | 10/1999 | Augustine | 602/2 |

FOREIGN PATENT DOCUMENTS

94/00090  1/1994  WIPO ..................... 607/114

*Primary Examiner*—Robert L. Nasser
*Attorney, Agent, or Firm*—Gray Cary Ware Freidenrich

[57] ABSTRACT

A wound treatment apparatus is provided which includes a thermally conductive bandage, a heater disposed against the bandage, aligned with a wound treatment area, an adhesive attachment device acting between the heater and the bandage, and a controller that controls the operation of the heater in order to provide a normothermic therapy to a wound. The normothermic therapy includes maintaining the temperature of tissue at the wound and/or near the wound in a range of about 36° C. to 38° C. The controller operates the heater by turning it on and off in a manner that cycles the heater's temperature.

20 Claims, 15 Drawing Sheets

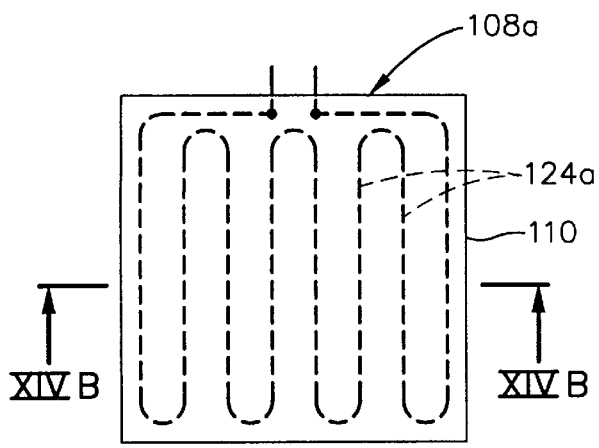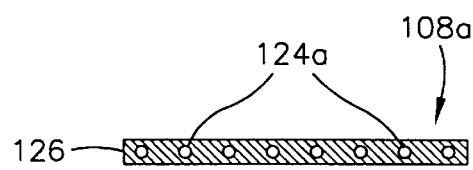
FIG. 14A
FIG. 14B
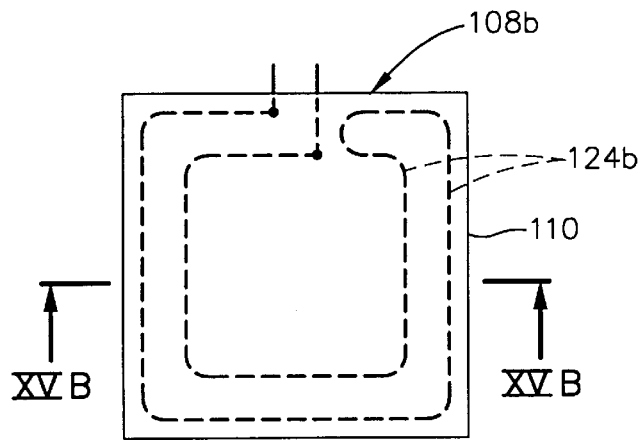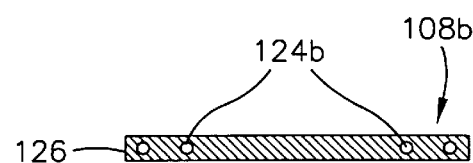
FIG. 15A
FIG. 15B
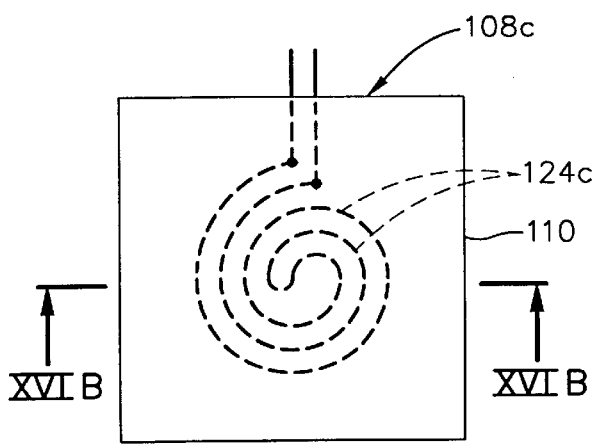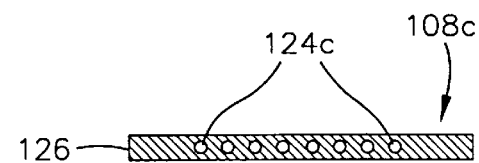
FIG. 16A
FIG. 16B

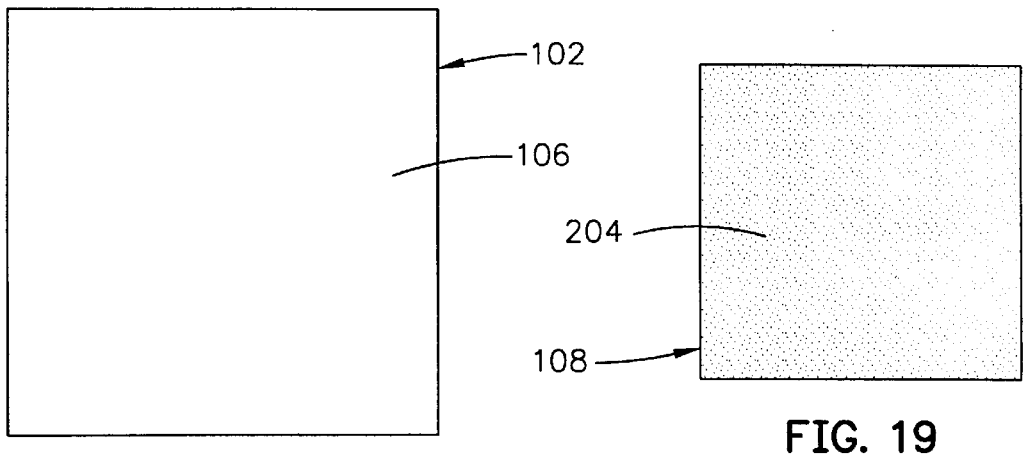
FIG. 18
FIG. 19
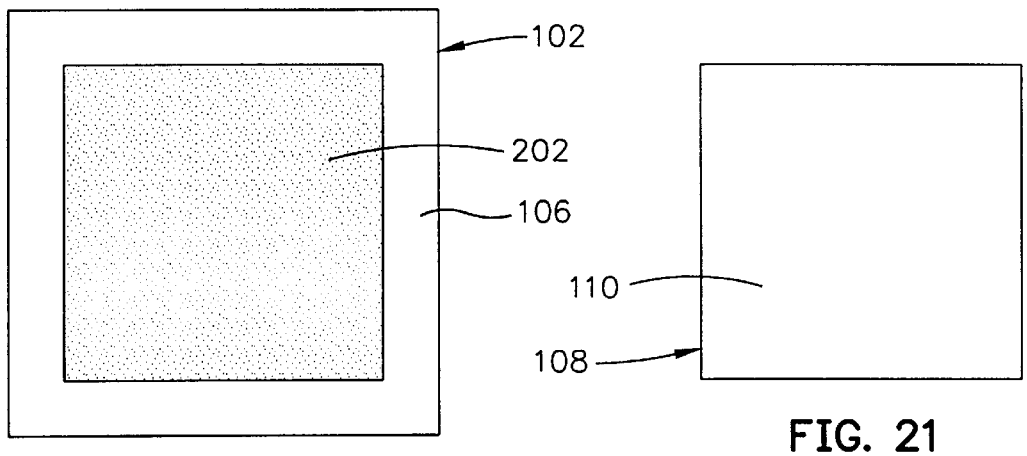
FIG. 20
FIG. 21
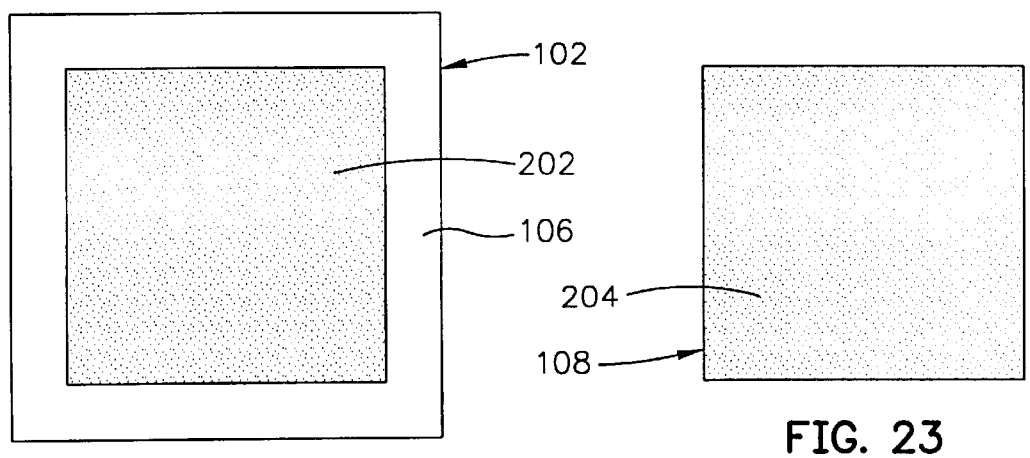
FIG. 22
FIG. 23

WOUND TREATMENT APPARATUS FOR NORMOTHERMIC TREATMENT OF WOUNDS

This application also contains material related to the following commonly assigned U. S. Patent Applications, which were concurrently filed with this application:

Ser. No. 09/056,191 filed Apr. 6, 1998 for "WOUND TREATMENT APPARATUS WITH HEAT SPREADING DEVICE";

Ser. No. 09/055,725 filed Apr. 6, 1998 for "WOUND TREATMENT APPARATUS WITH INFRARED ABSORPTIVE WOUND COVER";

Ser. No. 09/056,063 filed Apr. 6, 1998 for "WOUND TREATMENT APPARATUS WITH IR-TRANSPARENT OR IR-TRANSMISSIVE WOUND COVER"; and Ser. No. 09/055,597 filed Apr. 6, 1998 for "WOUND TREATMENT APPARATUS WITH A HEATER ADHESIVELY JOINED TO A BANDAGE".

STATEMENT OF REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention relates to a wound treatment device with a bandage and heater that are essentially planar, yet flexible, and are connected or joined by an attachment device that promotes heat transfer from the heater through the bandage to a wound treatment area where the temperature of tissue is maintained by control of the heater's operation in a normothermic temperature range.

2. Description of the Related Art

Wounds, in general, are breaks in the integrity of the skin of a patient. A first type of wound may result from mechanical trauma that produces a cut, tear, or an abrasion. There are many instruments of causality for such wounds, including knives, glass, gravel, or a scalpel. A second type of wound may be caused by a combination of heat and pressure wherein the heat alone is insufficient to cause an outright burn. Such wounds include pressure sores, decubitu; ulcers, or bed sores, and reflect an injury that is chronic in nature. A wound may also be vascular in origin. In this third type of wound, blood flow through a region may be altered sufficiently to cause secondary weakening of tissues which are eventually disrupted, thus forming a wound. In the case of arterial causes, the primary difficulty is getting oxygenated blood to the affected area. For venous causes, the primary difficulty is fluid congestion in the affected area which backs up, decreasing the flow of oxygenated blood. Because these wounds manifest underlying chronic disease processes, such as atherosclerotic vascular disease, congestive heart failure, and diabetes, these vascular injuries also are chronic in nature, forming wounds with ulcerated bases.

Heat therapy has been used to treat wounds since the days of Hippocrates, with varying results. Up to now, heat therapy for wounds has involved the application of heat under conditions that make the tissues of a wound hyperthermic. Hyperthermia impedes wound healing and may actually damage the wound tissues.

The "normal" range of temperature for the human body is 37° C.±1° C. (36° C.–38° C.). This is termed the "normothermic" range. Humans exhibit a thermoregulatory response to core temperature changes as little as ±0.1° C., wherein "core" as used herein refers to interior portions of the body. This extremely tight temperature control is necessary because virtually all cellular functions, chemical reactions and enzymatic reactions are optimum at normothermia.

Surface tissue varies in temperature according to where on the body it is located. The skin of the torso is usually hypothermic, while the skin of the legs is always hypothermic. The normal skin temperature of the distal leg is approximately 32° C., which is considered to be "moderately hypothermic". The skin temperature of the distal leg of a patient with vascular insufficiency may be as low as 25° C., which is "severely hypothermic". The hypothermic condition of wounds and ulcers inhibits healing. Severely hypothermic skin or wound tissue is in a state that may be termed "suspended animation". In suspended animation, tissue is living, but cellular functions necessary for cell division and collagen deposition are slowed or even stopped. Further, the immune system is inhibited, allowing wounds to become heavily colonized with bacteria. The local application of heat to hypothermic skin will cause some degree of vasodilatation, resulting in an increase in local blood flow. Increased blood flow increases the subcutaneous oxygen tension ($PsqO_2$) which, in turn, increases both collagen deposition and immune function.

Many references report that the immune system is inhibited by hypothermia and activated by mild hyperthermia (fever). Persp Biol Med:439–474, Spring 1980, reports that local body temperature is a critical factor determining host susceptibility, the location of lesions and contracting infectious diseases. New Eng J Med 305:808–814, 1981, reports that animals exposed to cold environments are more susceptible to infectious diseases, whereas exposure to high ambient temperatures often produces a beneficial result. Wound Rep Reg 2:48–56, 1994 and Acta Anaesth Scand 38:201–205, 1994, report that infections caused by a standard inoculum of e. coli or s. aureus were significantly more severe in hypothermic guinea pigs than in normothermic control animals. New Eng J Med 334:1209–1215, 1996, reports that hypothermic colorectal surgical patients had three times more wound infections (19% vs. 6%) than those who were kept normothermic during surgery with a Bair Hugger® patient warming system described in commonly assigned U.S. Pat. Nos 5,324,320, 5,300,102 and 5,350,417. Further, six weeks of warming therapy with the Bair Hugger® patient warming system has successfully healed chronic progressive ulcers which heretofore have been resistant to antibiotic therapies.

As stated hereinabove, enzymatic reactions are promoted by normothermia. Both platelet adhesion and the clotting cascade result from a series of enzymatic chemical reactions. Research efforts have been reported that show hypothermic patients bleeding more than normothermic patients. J Thorac Cardiovasc Surg 104:108–116, 1992, and Ann Surg 205:175–181, 1987, report that skin cooling produces a reversible platelet dysfunction and prolonged bleeding times. Lancet 347 (8997):289–292, 1995, reports that mildly hypothermic total hip arthroplasty patients lost an average of 500 ml more blood and had an 88% higher incidence of transfusion than patients who were kept normothermic with the aforementioned Bair Hugger® Patient Warming System. Anesthesiology 85: A66, 1996, reports that hypothermic liver transplant patients required twice as many units of blood (18.6 vs. 9.8) and 57% more units of all blood products (46.2 vs. 29.4) than patients who were kept normothermic with the Bair Hugger® Patient Warming System.

When used to treat wounds; heat has been applied at higher than normothermic temperatures, with the goal of making the wounds mildly hyperthermic. These higher temperatures have often resulted in increasing tissue damage, rather than promoting wound therapy and healing.

Currently available medical devices that apply heat to wounds include infrared lights, warm water pads, warm water bottles, whirlpools and Sitz baths. All types of lesions, such as surgical, chronic, traumatic, donor sites, infected wounds and burns, have been treated with these warming modalities. Particularly difficult has been the application of heat to open wounds such as ulcers. Treatment of a wound with infrared light requires that the wound be positioned under the light during therapy, necessitating patient immobility. Further, the infrared heat causes wounds to dry, thereby slowing the healing process. Warm water pads and bottles and electrical heating pads are cumbersome, reduce patient mobility, and are usually applied to the extremities and held in place with inconvenient wraps such as straps, hook-and-eye material or tabs. Whirlpools and Sitz baths reduce mobility and limit the duration of warming therapy due to skin maceration by the water. None of these modalities is capable of prolonged, uniform, normothermic heat treatment of a wound.

SUMMARY OF THE INVENTION

There is a need for a wound treatment apparatus to conveniently treat a wound by raising the temperature of wound and/or periwound tissue toward normothermia, while allowing patient mobility. It is also important that the wound treatment apparatus be flexible and have a low profile for convenience of the patient. Such an apparatus should be thermally conductive for efficient heat transfer, be convenient to operate without adversely impacting the patient, and be capable of maintaining a moist wound environment.

Preferably, the operation of the wound treatment apparatus is referred to a "wound treatment area" (or "treatment area") that may include the wound, unwounded skin adjacent the wound (the periwound), or both.

One purpose of this invention is to raise the wound tissue and/or periwound tissue temperatures toward normothermia to promote a more optimal healing environment. The present invention is not a "heating therapy", per se, where it is the intent of "heating therapy" to heat the tissue above normothermia to hyperthermic levels. Rather, the present invention is intended to bring the wound and periwound tissues towards normothermia, without exceeding normothermia.

This invention is also designed to elevate the temperature of the hypothermic skin and subcutaneous tissue of the selected treatment area to a temperature which is close to normothermia. The purpose of this is to create within the wound and periwound tissues of the selected treatment area a more normal physiologic condition, specifically a more normothermic condition, which is conducive to better wound healing. This invention contemplates the use of an active heater to deliver heat to a wound, but the role of the heater can better be described as "guarding" against heat loss by providing a heat source to counteract the effects of heat loss.

The concept of a "guard heater" is straightforward. The guard heater is heated to approximately the same temperature as the adjacent heated body. Since heat must flow down a temperature gradient, it can only be lost to a cooler surface. The guard heater is not cooler than the adjacent body and, therefore, cannot accept heat from the adjacent body. The normal temperature gradient for tissue goes from about 37° C. deep in the body's core down to about 32° C. at the skin's surface. With a guard heater in place, heat loss directly from the wound and periwound tissue surfaces is markedly diminished. This decrease in local heat loss provides for the zone of 37° C. core temperature to move outward toward the skin, narrowing the gradient from core temperature to surface temperature as the zone of core temperature approaches the surface in the area of the guard heater. The guard heater behaves very much like a perfect insulator, providing a circumstances suitable for warming of the wound with heat flowing from the core. The guard heater of the present invention has an additional advantage over near-perfect passive insulation in that near-perfect insulation would require the use of several inches of bulky insulating material. Such bulkiness in a wound dressing is not practical for proper wound care.

The "guard" heater of the present invention, for example, in use on wounds below the knee where vascular insufficiency may occur, operates from above ambient temperature to 38° C., which includes the range of "normothermia". Obviously, because of the thermal mass of the leg, the blood flow through the leg and inherent inefficiencies of heat transfer, the resulting wound and periwound tissue temperatures usually remain less than the operating temperature of the "guard" heater, and probably less than the patient's core temperature.

In order to deliver normothermic heat therapy to a wound treatment area it would be beneficial to employ standard bandages that are available for wound treatment. In this case, a heater may conveniently be placed on top of a bandage and the heater/bandage apparatus may be placed on the wound treatment area. However it is necessary that the treatment apparatus apply and/or maintain the heat generated by the heater within a normothermic temperature range of about 36° to about 38° C.

Finally, we have determined that a controller is desirable for operating the heater so that the normothermic heat therapy is implemented at the treatment area.

The present invention enables normothermic heat therapy of wounds by a wound treatment apparatus that includes four components: a thermally conductive bandage, a heater, an attachment device for connecting or joining the bandage and heater, and a controller. The heater is in thermal contact with the bandage over a treatment area and the attachment device maintains the contact. The antecedent attachment device is fashioned so that, during contact, conduction of heat between the heater and the bandage is maximized and, upon removal of the heater from the wound cover, the bandage remains attached to the person's body. Preferably, the heater and bandage are planar, so as to maintain a low profile for the convenience of the patient, and are flexible, so as to conform to the wound and to the contour of the patient's body at and near the wound.

The bandage is preferably thermally conductive. Thermally conductive bandages may be made of such materials as hydrogels, hydrocolloids, moist gauze, moist foam, hydrated alginates and polymeric films. In a preferred embodiment, an upper surface of the bandage includes a layer of moisture-impermeable material. With this arrangement, the bandage protects and maintains the humidity of the wound bed and the adjacent tissue.

The heater includes means for generating heat that may take the form of, for example, an electrical resistance element embedded or laminated in a layer of flexible material. The heater may also operate by chemical, phase-change, or hot water means.

The attachment device may be made of a layer of polymeric film with a layer of adhesive applied to both sides which is commonly referred as "two-faced tape" or "double-sided tape". In another embodiment, a layer of adhesive is applied to a surface of the bandage and/or the heater. The attachment device may be continuous across the entire treatment area so that uniform bonding will promote uniform conductive heat transfer from the heater to the bandage. The attachment device employs an adhesive in contrast to straps, hook-and-eye material or tabs. These latter devices allow air spaces to develop between the heater and the bandage resulting in poor and unpredictable heat transfer to the wound.

The controller controls the operation of the heater, maintaining the temperature of the heater in a normothermic temperature range. The controller may maintain such operation on a continuous, or an intermittent basis. Preferably, the controller is programmable, and includes programming or logic to control heater operational parameters including temperature, duty cycle, and therapy cycle.

An object of the present invention is to provide an apparatus for treating a wound by maintaining the temperature of tissue in and/or near the wound in a normothermic range.

Another object is to maintain the temperature of tissue in and/or near the wound in a range of about 36° C. to 38° C.

A further object is to maintain the temperature of tissue in and/or near the wound in a range of near ambient to about 38° C.

Still another object is to provide a low profile, flexible wound treatment apparatus that includes a heater attached to a bandage and a controller connected to the heater for operating the heater so that the apparatus provides a normothermic therapy regime to a wound.

Other objects and advantages of the invention will become apparent upon reading the following description taken together with the accompanying drawings.

DESCRIPTION OF THE DRAWINGS

FIG. 14A is a planar illustration of an electrical resistance element embedded in a flexible layer for uniform heating;

FIG. 14B is a view taken along plane XIVB—XIVB of FIG. 14A;

FIG. 15A is a planar view of an electrical resistance element embedded in a flexible layer for heating a portion of a treatment area;

FIG. 15B is a view taken along plane XVB—XVB of FIG. 15A;

FIG. 16A is a planar view of an electrical resistance element embedded in a flexible layer for uniform heating of a central portion of a treatment area;

FIG. 16B is a view taken along plane XVIB—XVIB of FIG. 16A;

FIG. 18 is a view taken along plane XVIII—XVIII of FIG. 17;

FIG. 19 is a view taken along plane XIX—XIX of FIG. 17;

FIG. 20 is a view taken along plane XX—XX of FIG. 17;

FIG. 21 is a view taken along plane XXI—XXI of FIG. 17;

FIG. 22 is a view taken along plane XXII—XXII of FIG. 17;

FIG. 23 is a view taken along plane XXIII—XXIII of FIG. 17;

DESCRIPTION OF THE PREFERRED EMBODIMENTS

Figure 1:
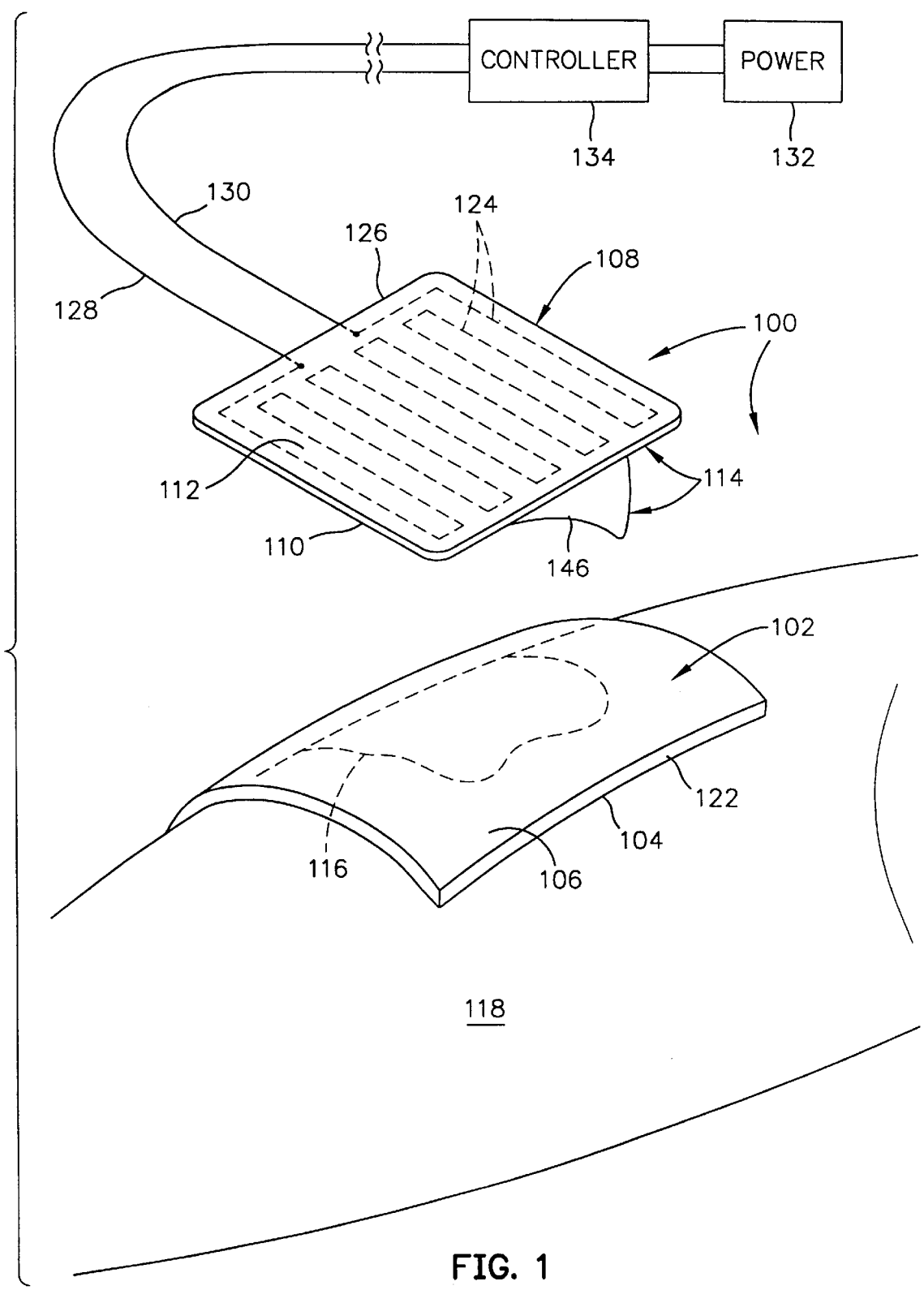
FIG. 1 is an isometric view of a first embodiment of the wound treatment apparatus being applied to a wound on a person's body.

Referring now to FIGS. 1–31, wherein like reference numerals designate like or similar parts throughout the several views there are shown various embodiments of a wound treatment apparatus in according to the invention.

Figure 2:
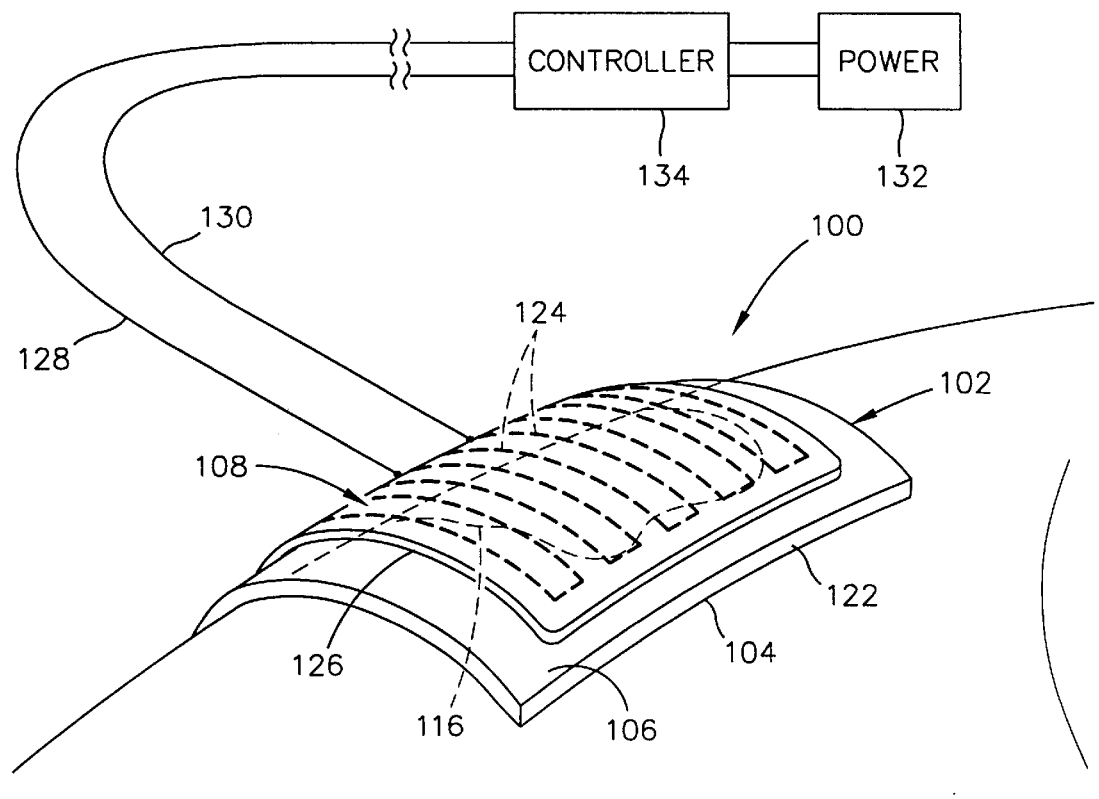
FIG. 2 is an isometric view of the wound treatment apparatus applied to the wound on the person's body.
Figure 3:
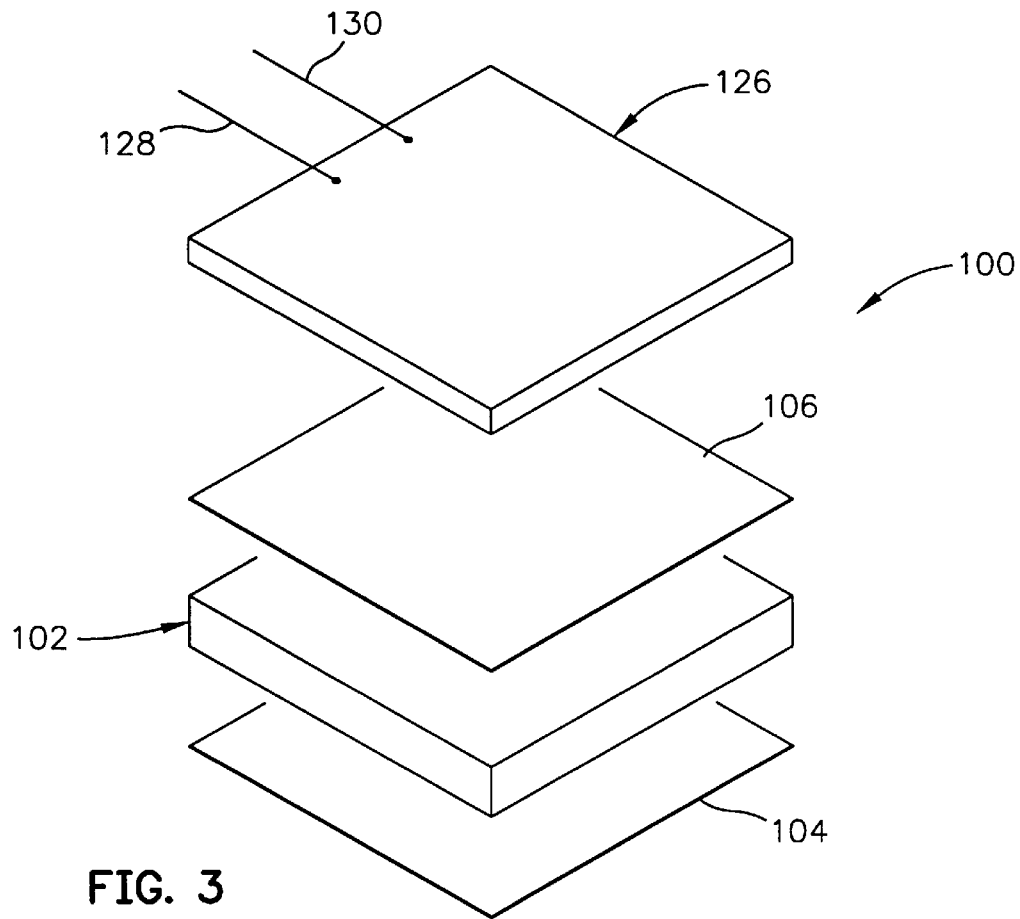
FIG. 3 is an exploded isometric view of the wound treatment apparatus.
Figure 4:
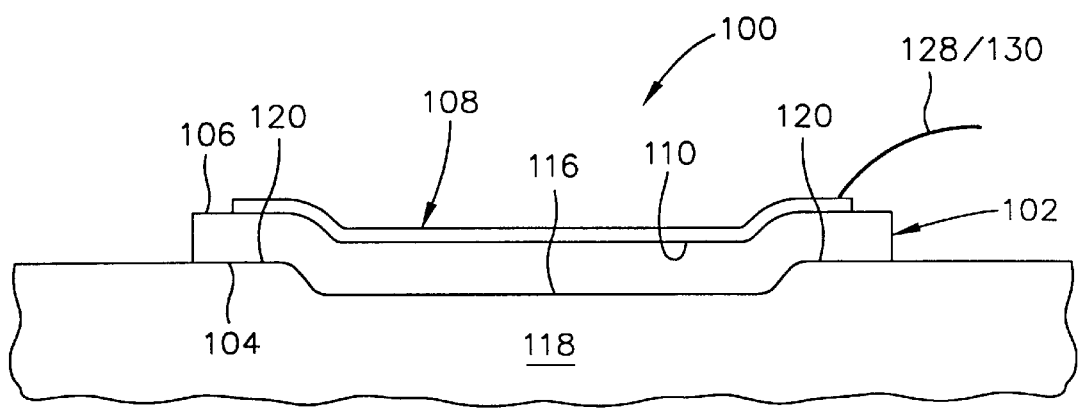
FIG. 4 is a cross-sectional view of the wound treatment apparatus applied to the wound on the person's body.

As shown in FIGS. 1–6, one embodiment of the wound treatment apparatus 100 includes a thermally conductive bandage 102 which has first (lower) and second (upper) surfaces 104 and 106, a heater 108 which has first (lower) and second (upper) surfaces 110 and 112 and an attachment device 114 for joining the heater 108 and the bandage 102 in such a manner as to transfer heat from the heater 108 to the bandage 102. Preferably, the attachment device maintains surface-to-surface contact between the second surface 106 of the bandage 102 and the first surface 110 of the heater. In FIGS. 2 and 4, the wound treatment apparatus 100 is shown in peace covering a wound 116 of a person's body 118, the wound being shown depressed. Immediately adjacent the wound is a periwound area 120 which is typically a peripheral band of tissue around the wound area with less trauma than the tissue of the wound area. As will be explained in more detail hereinafter, the wound treatment apparatus is capable of treating a wound treatment area that includes the wound and/or the periwound area, as desired.

Figure 5:
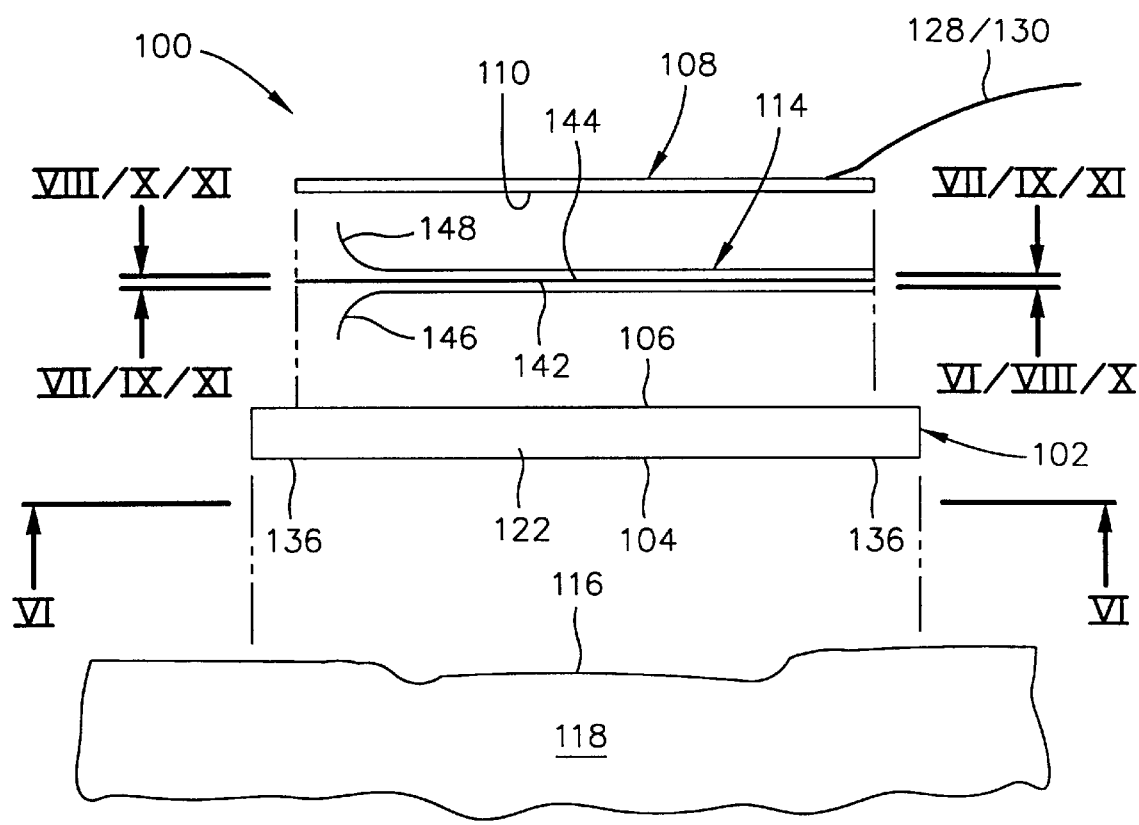
FIG. 5 is an exploded cross-sectional illustration of an embodiment of the invention above the wound area of the person's body.

The second surface 106 of the bandage preferably comprises a sheet of smooth material. In a preferred embodiment, this surface may be provided by a polymeric film. A layer 122 of hydrogel, hydrocolloid, or hydrated alginate may be affixed to the polymeric film 106 by any suitable means, such as an adhesive, and may provide the first surface 104. It is preferred that any of these combinations provide the bandage with high thermal conductivity and maintain a moist environment at the wound. In the layer 122, a foam or gauze may be used in lieu of the compounds enumerated above. If the gauze or foam provides the first surface 104, the gauze or foam will absorb moisture from the wound, providing the desired heat conductivity and moist environment. Alternatively, the bandage 102 may simply be a single layer or film of a heat-conductive polymer so as to optimize heat conductivity of the bandage. In any embodiment of the bandage, it is preferred that the bandage be planar, as shown in FIGS. 3 and 5, and be flexible to conform to the wound 116 as shown in FIG. 4, as well as the person's body, as shown in FIGS. 1 and 2.

In the embodiment 100 of the wound treatment apparatus, the heater 108 includes means for generating heat that may be electrically operated. For example, the means may take the form of an electrical resistance element 124 which is embedded in or laminated to a flexible planar member 126, made from a material such as polyethylene, silicon, rubber or flexible cloth. In the preferred embodiment, the heater 108 is substantially planar, as shown in FIGS. 1, 3 and 5, and yet flexible in order that it conform, with the bandage, to the wound 116, as shown in FIG. 4, and to the person's body as shown in FIGS. 2 and 4. As will be explained in more detail hereinafter, the adhesive attachment device 114 joins the heater 108 to the bandage 102, as shown in FIG. 4, so as to maximize heat transfer between the heater 108 and the bandage 102.

As illustrated in FIGS. 1 and 4, the electrical resistance element 124 is connected to first and second electrical conductors 128 and 130, which are connected to an electrical power source 132, via a controller 134. The purpose of the controller 134 is to control electrical power provided to the electrical resistance element 124 to maintain a normothermic environment at the wound 116. As shown in FIGS. 1 and 2, the electrical resistance element 124 may extend back and forth in the flexible layer 126 with a desired spacing to promote uniform heating of the bandage 102.

Figure 6:
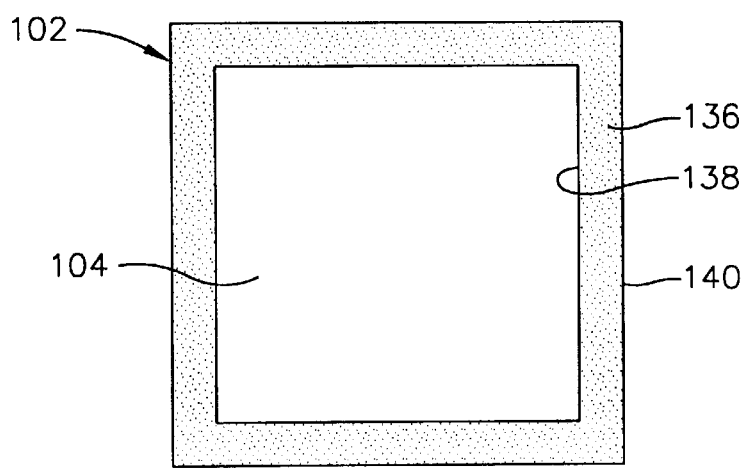
FIG. 6 is a view taken along plane VI—VI of FIG. 5.

As shown in FIG. 6, the first surface 104 of the bandage 102 is provided with an open pattern of adhesive 136 at or near its periphery. The adhesive pattern 136 may completely encompass the wound and the periwound area so as to trap the natural moisture of the body which, in turn, moistens the layer 122 of the bandage, or otherwise maintains a moist environment across the wound treatment area for wound therapy purposes. Accordingly, the pattern of adhesive 136 has inner and outer boundaries 138 and 140 wherein, in the preferred embodiment, the outer boundary 140 coincides with the outer perimeter of the bandage. It should be understood that the bandage 102, the heater 108, and the pattern of adhesive may take various shapes, such as the square, shown in the drawings, or a rectangle, circle or ellipse, or any other regular or irregular shape, depending upon various shapes of wound treatment areas.

The preferred adhesive attachment device 114 is a double-sided tape, as shown in FIG. 5. It is preferred that the double-sided tape be a polymeric film with first and second surfaces with first and second layers of adhesive 142 and 144 thereon. The double-sided tape comes with first and second release liners 146 and 148 which are removed so that the adhesive layers 142 and 144 can be joined to the second surface 106 of the bandage 102 and to the first surface 110 of the heater 108, respectively, as shown in FIGS. 1, 4 and 5. In FIG. 1, the release liner 146 is partially removed from the adhesive layer 142 (see FIG. 5) in preparation for attaching the heater 108 to the second surface 106 of the bandage 102. The double-sided tape 114 is very flexible and conducts heat between the heater 108 and the bandage 102. It is preferred that the planar dimensions of the double-sided tape 114 be the same as the planar dimension of the heater 108 so as to transfer heat from the entire first surface 110 of the heater 108 to the bandage 102. It should be noted that, because of the polymeric film 1106 forming the second surface of the bandage 102, transfer of heat by conduction to the bandage 102 is promoted.

Figure 7:
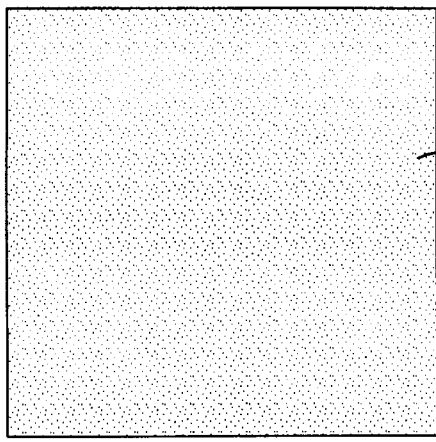
FIG. 7 is a view taken along plane VII—VII of FIG. 5.
Figure 8:
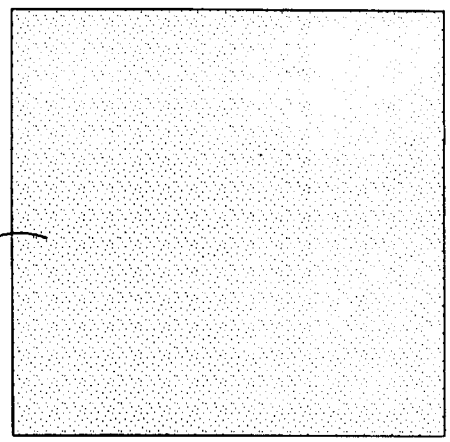
FIG. 8 is a view taken along plane VIII—VIII of FIG. 5.

When heat therapy is interrupted or terminated, it may be desirable to detach the heater 108 from the bandage 102. In this regard, the heater 108 is preferably detachably joined to the bandage 102. Detachment in the embodiment just described will necessitate pulling the heater 108 away from the bandage 102, thereby subjecting each adhesive layer therebelow to a pull force. In order for the bandage 102 to remain in place while the heater 108 is being removed, the pull strength of the attachment device 114 must be less than the pull strength of the pattern adhesive 136. Various means for achieving this objective with double-sided tape are shown in FIGS. 7–12. FIGS. 7 and 8 show the adhesive layers 142 and 144 completely covering the surfaces of the polymeric film. One of these surfaces will be required to have less pull strength than the pull strength of the pattern of adhesive 136. In a preferred embodiment, the adhesive layer 142 has less pull strength than each of the pattern of adhesive 136 and the adhesive layer 144, allowing the heater 108 to be removed from the bandage 102 without leaving any adhesive on the bandage. This may be accomplished by employing an adhesive layer 142 which is less tacky than each of the pattern of adhesive 136 and the adhesive layer 144. Less tack can be achieved by doping the same adhesive with a solvent or inert filler, such as talcum or chalk, or employing another adhesive with a tack known to be less than the tack of the adhesives 136 and 144. If it is desired to leave the adhesive on the bandage 102, then the roles of the tack would be switched between the adhesive layers 142 and 144.

Figure 9:
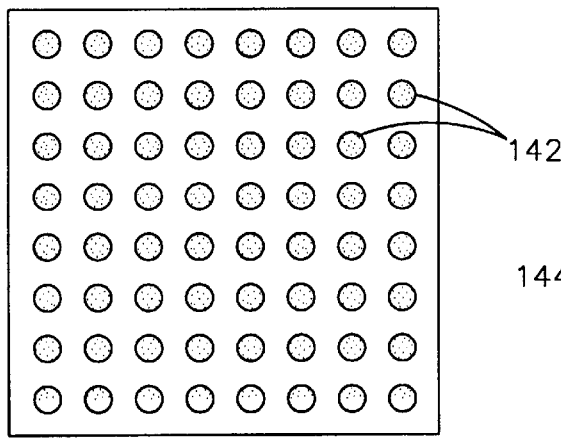
FIG. 9 is a view taken along plane IX—IX of FIG. 5.
Figure 10:
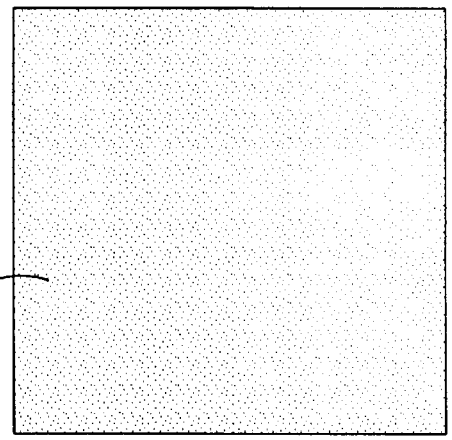
FIG. 10 is a view taken along plane X—X of FIG. 5.
Figure 11:
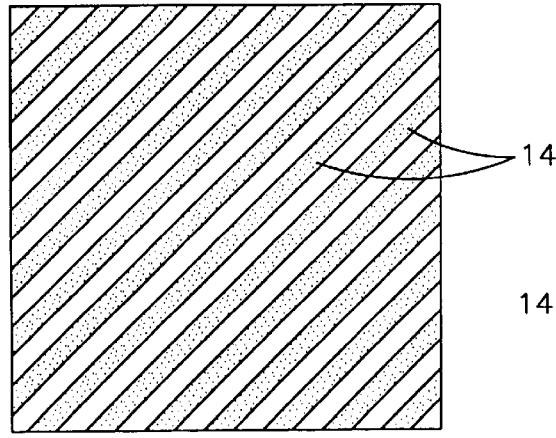
FIG. 11 is a view taken along plane XI—XI of FIG. 5.
Figure 12:
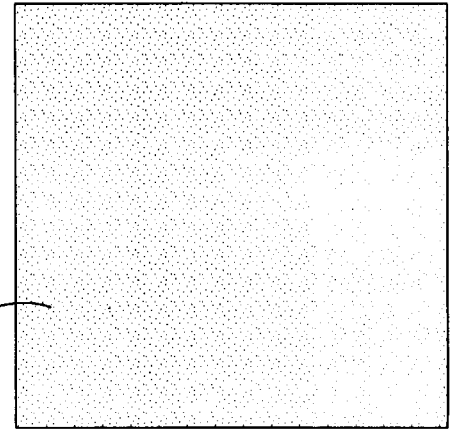
FIG. 12 is a view taken along plane XII—XII of FIG. 5.

Lower pull strength of the adhesive between the heater 108 and the bandage 102, as compared to the pull strength of the adhesive attaching the bandage 102 to a person's body, can be provided by intermittent adhesive patterns such as the circular regions 142i shown in FIG. 9. In contrast, as shown in FIG. 10, the adhesive layer 144 would be an entire plane so that when the heater is pulled, the double-sided tape leaves with the heater 108 rather than being retained on the bandage 102. As shown in FIG. 9, the adhesive regions 142i may be numerous circular dots of adhesive which are sized and spaced from one another in a matrix to provide a pull strength of the adhesive attachment device that is less than the pull strength of the pattern of adhesive 136 and less than continuous adhesive layer 144. With this arrangement, the same adhesive may be used for the adhesive layers 142 and 144 of the double-sided tape and the pattern of adhesive 136 on the bandage. Again, the layers 142 and 144 of the double-sided tape 114 may be switched if it is desired to leave the double-sided tape on the bandage 102 when the heater 108 is pulled therefrom. Another intermittent adhesive pattern is shown at 142s in FIG. 11, wherein diagonal spaced-apart strips of adhesive material are provided across the polymeric film. Here again, the sizing of the strips and their spacing from one another are arranged so that the pull strength of the adhesive attachment device is less than the pull strength of each of the body adhesive layer 136 and the full plane adhesive layer 144 in FIG. 12. It should be understood that the intermittent adhesive structure may take various patterns in order to achieve the desired reduction in pull strength. The spacing between the intermittent layers should be made as small as possible so as to promote conductive heat transfer between the heater 108 and the bandage 102.

Figure 13:
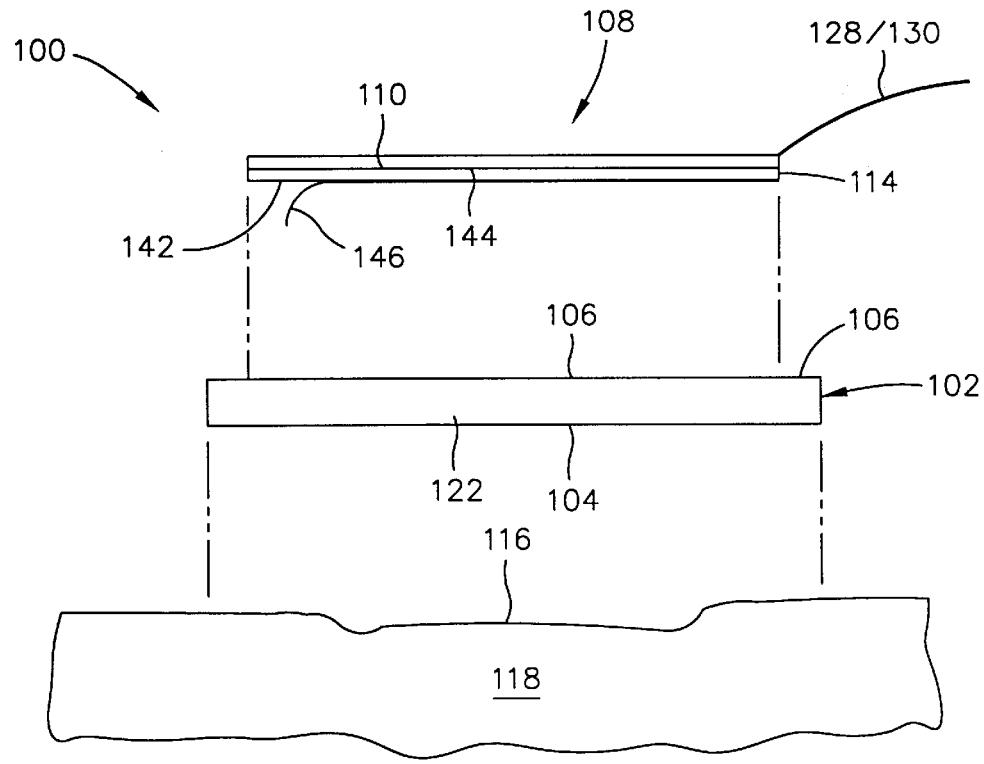
FIG. 13 is an exploded cross-sectional view of the first embodiment of the wound treatment apparatus after attaching an attachment device to the heater.

In FIG. 13 the adhesive layer 142 of the double-sided tape has been applied to the first surface 110 of the heater 108 and the release liner 146 has been partially removed from the first adhesive layer 142, similar to the showing in FIG. 1. The heater 108 may be supplied with the double-sided tape in place, as shown in FIG. 13, or may be supplied separately as described and shown in FIG. 5.

Manifestly, an attachment device should permit the heater and bandage to be joined in such a way as to maximize heat transfer therebetween while permitting the heater to be detached from the bandage without detaching the bandage from the skin. While various adhesive configurations are shown for this purpose, it is contemplated that other attachment mechanisms could be used.

FIGS. 14–16 illustrate various embodiments of electrical resistance heaters 108. In the heater 108a shown in FIG. 14A, and electrical resistance element 124a winds back and forth within the flexible planar member 126, similar to what is shown in FIG. 1. The spacing between the windings of the electrical resistance element 124a may be sized so as to ensure substantially uniform heating. FIG. 14B shows the electrical resistance element embedded or laminated in the flexible planar member 126. In FIG. 15A, the electrical resistance element 124b takes a path along a peripheral zone of the flexible planar member 126, so that the periphery of the heater 108b is uniformly heated to a temperature greater than a central portion of the heater. Again, these electrical resistance elements 124b are shown embedded or laminated in the flexible planar member 126 in FIG. 15B. In FIG. 16A, the electrical resistance element 124c takes a spiral path out and back within a central region of the heater 108c so as to uniformly heat the central region of the heater to a higher temperature than regions outbound therefrom. The heater 108a is adapted for applying heat to both the wound and periwound area 116 and 120 in FIG. 4, the heater 108b is adapted for applying heat principally to the periwound area 120, and the heater 108c is adapted for applying heat principally to the wound 116.

Figure 17:
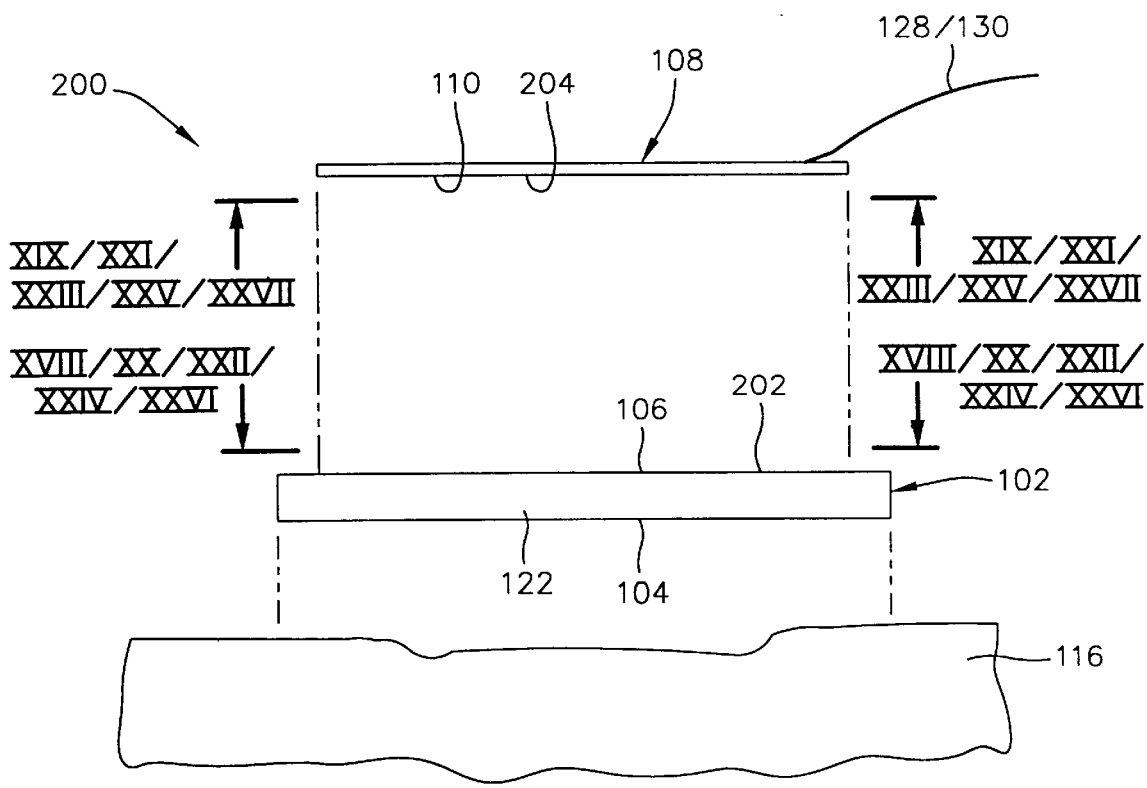
FIG. 17 is an exploded cross-sectional view of another embodiment of the invention shown above a wound area.

Another embodiment 200 of the wound treatment apparatus is illustrated in FIG. 17, wherein an adhesive layer 202 is on the second surface 106 of the bandage 102 and/or an adhesive layer 204 is on the first surface 110 of the heater 108. Various embodiments of these attachment devices are illustrated in FIGS. 18–28. The first embodiment of the attachment device is shown in FIGS. 18 and 19, wherein the heater 108 is provided with the adhesive layer 204 and the bandage 102 is not provided with any adhesive layer. In FIGS. 20 and 21, the situation is reversed wherein the bandage 102 is provided with the adhesive layer 202 and the heater 108 does not have an adhesive layer. FIGS. 22 and 23 illustrate a still further embodiment wherein the bandage 102 is provided with the adhesive layer 202 and the heater 108 is provided with the adhesive layer 204. The adhesive layers 202 and 204 in FIGS. 22 and 23 may be made from an adhesive which will bond only when these two adhesive layers are placed in contact with one another. Otherwise, the adhesive layer 204 will not bond to the polymeric surface surrounding the adhesive layer 202, or any other surface including a person's skin. This scheme has an advantage from the standpoint that adhesive layers 202 and 204 on the bandage 102 and the heater 108, respectively, will not attach to anything until they are brought into contact between the heater 108 and the bandage 102. This promotes manufacturability, logistics and operation of the invention. A suitable adhesive for this purpose is 3M Acrylic Adhesive A40 (of the kind used in 3M Repositionable tape, product number 665). It is desirable that the pull strength of the adhesive attachment devices shown in FIGS. 18–23 be lower than the pull strength of the body adhesive 136 shown in FIG. 6. This can be accomplished by making the tack of the adhesive attachment device less than the tack of the pattern of adhesive 136.

Figure 24:
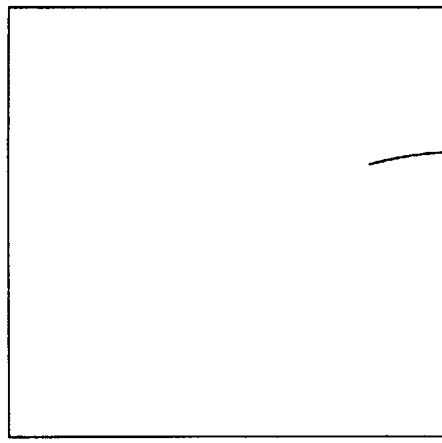
FIG. 24 is a view taken along plane XXIV—XXIV of FIG. 17.
Figure 25:
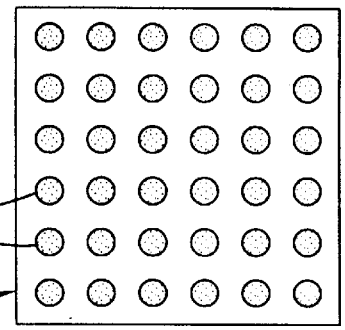
FIG. 25 is a view taken along plane XXV—XXV of FIG. 17.
Figure 26:
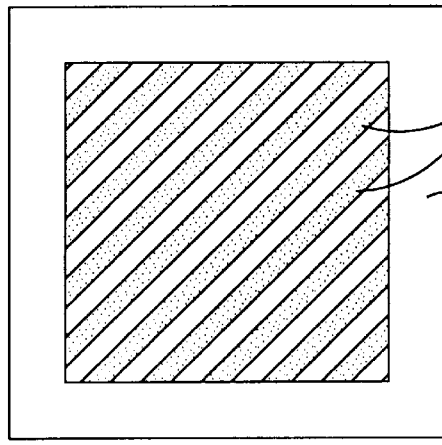
FIG. 26 is a view taken along plane XXVI—XXVI of FIG. 17.
Figure 27:
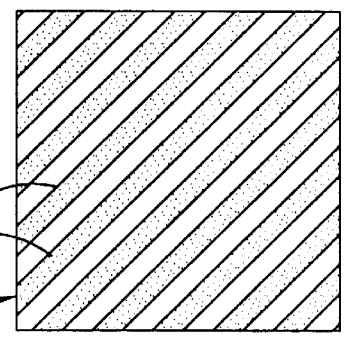
FIG. 27 is a view taken along plane XXVII—XXVII of FIG. 17.
Figure 28:
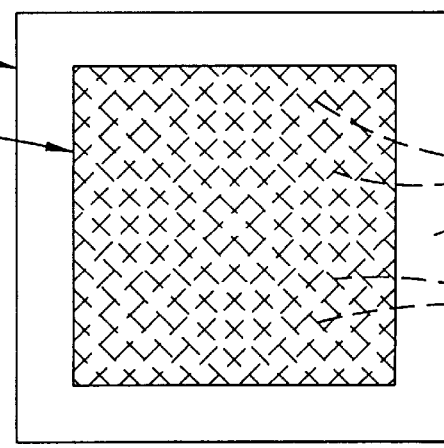
FIG. 28 is a view showing schematically the engagement of the intermittent adhesives shown in FIGS. 26 and 27.

Attachment devices employing intermittent adhesive patterns are shown in FIGS. 24–28. The embodiment in FIGS. 24 and 25 shows the heater 108 provided with circular spaced-apart adhesive regions 204c, while the bandage 102 is not provided with any adhesive. In the embodiment shown in FIGS. 26 and 27, each of the bandage 102 and the heater 108 is provided with diagonal spaced-apart adhesive strips 202d and 204d, respectively. When these adhesive strips are brought into contact with one another, as shown in FIG. 28, they criss-cross one another to provide the desired bonding between the heater 108 and the bandage 102.

The adhesive areas of the intermittent adhesive patterns shown in FIGS. 24–28 are sized and spaced from one another so that the pull strength of each attachment device is less than the pull strength of the pattern of adhesive 136 shown in FIG. 6, as discussed hereinabove. Again, the size of the intermittent adhesive patterns and the spacing therebetween should be tailored to maximize thermal conductivity between the heater 108 and the bandage 102 and yet ensure that the pull strength between the heater and the bandage is less than the pull strength between the bandage and the person's body.

Figure 29:
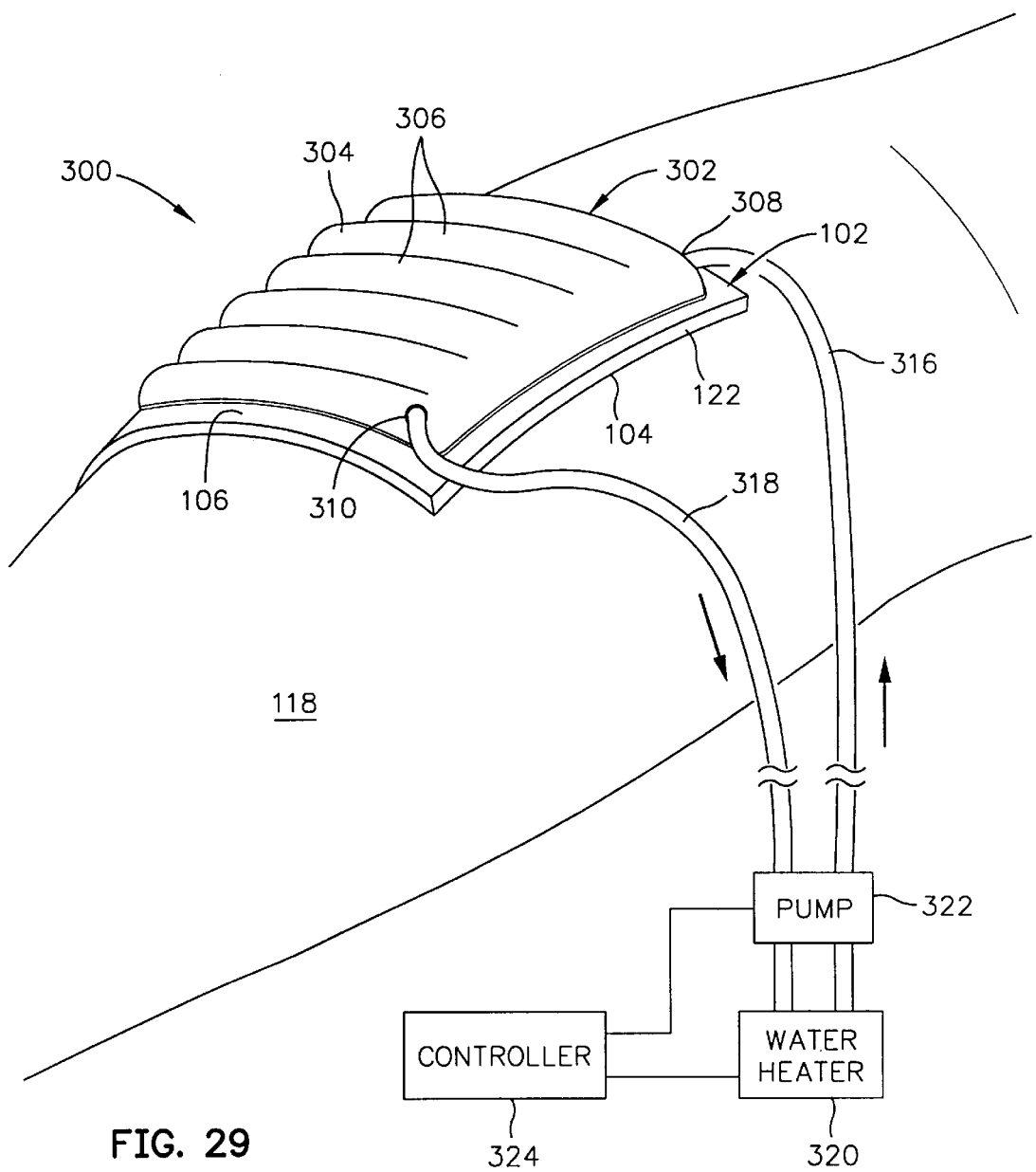
FIG. 29 is an isometric illustration of a further embodiment of the wound treatment apparatus applied to a wound on the person's body.
Figure 30:
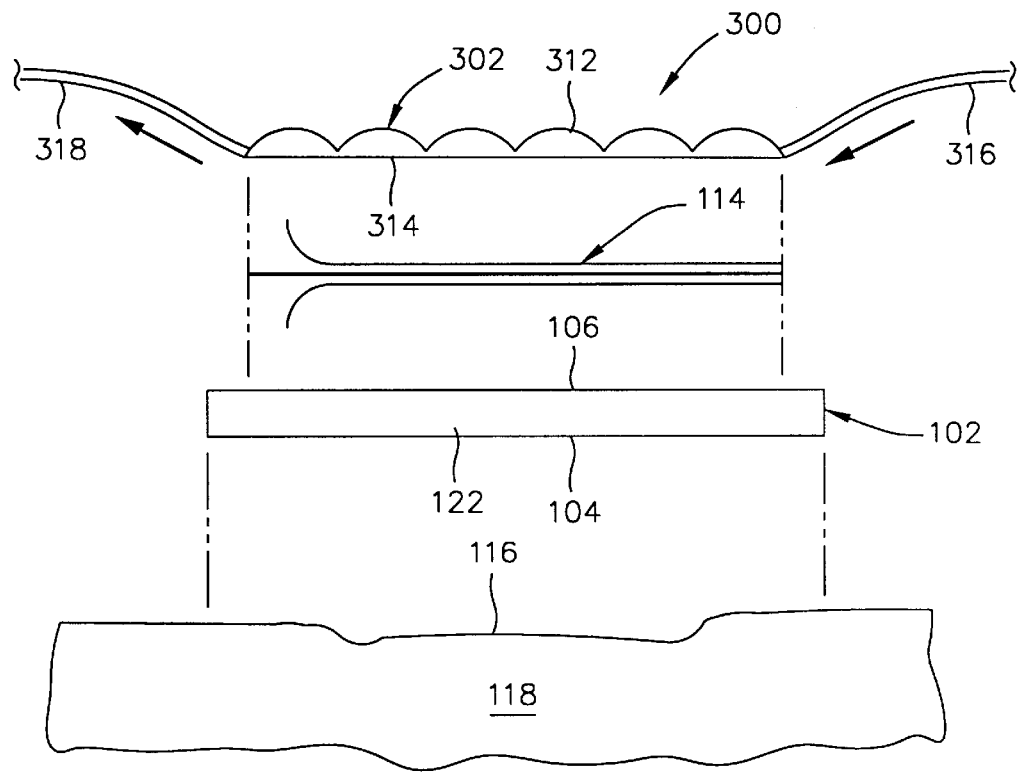
FIG. 30 is an exploded cross-sectional illustration of the apparatus shown in FIG. 29 shown above the wound.
Figure 31:
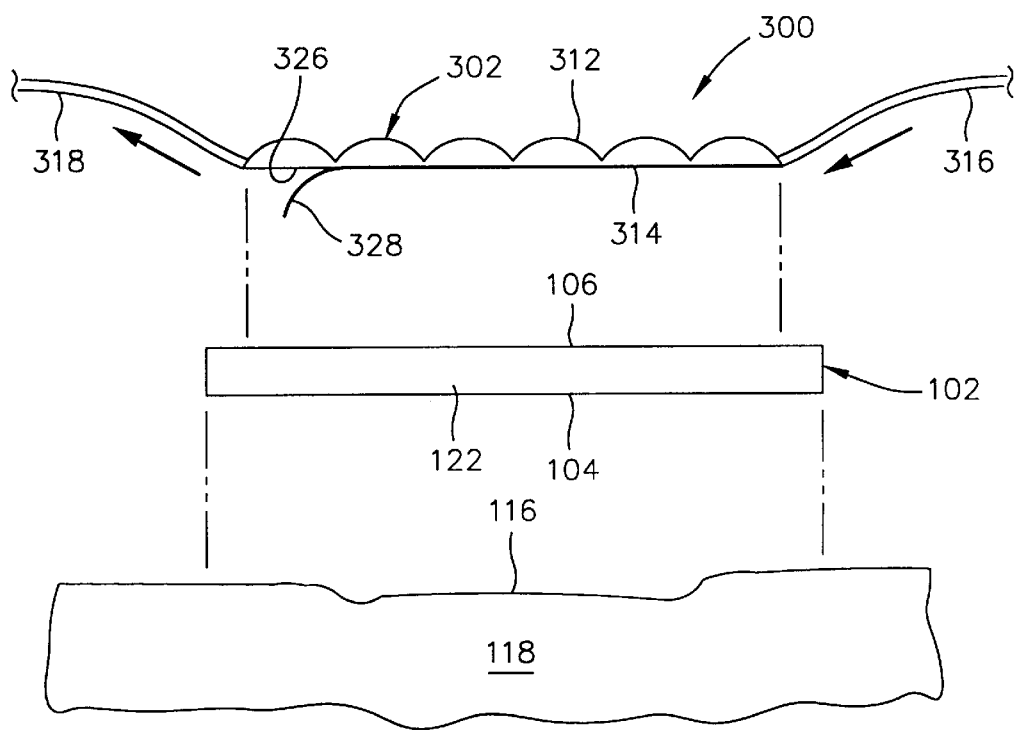
FIG. 31 is an exploded cross-sectional illustration of the FIG. 29 embodiment with an adhesive attachment device applied to the heater.

Another embodiment 300 of the wound treatment apparatus is illustrated in FIGS. 29–31. In this embodiment, a heater 302 employs heated water as the means for generating heat to be provided to the bandage 102 and then to a wound site covered by the bandage. The heater 302 may comprise a pouch 304 which has water channels extending back and forth in series from an inlet end 308 to an outlet end 310. The pouch 304 may be made by thermo-setting the periphery as well as channel lines of a pair of polymeric films 312 and 314 as shown in FIG. 30. The bottom film 314 may be stiffer than the top film 312. Heated water is supplied by inlet and outlet water lines 316 and 318 which are connected to a water heater 320 via a pump 322. A controller 324 is provided for controlling the temperature of the water in the water heater 320 and the amount of water pumped by the pump 322. The heated water is preferably maintained at such a temperature and flow rate that the wound site 116 is maintained at a normothermic temperature. The bandage 102 may comprise any of the aforementioned embodiments. Further, the attachment device for attaching the heater 302 to the bandage 102 may comprise any of the aforementioned adhesive attachment devices or any equivalent devices or arrangements that connect the heater and bandage for maximum thermal conductivity, yet allow detachment of the heater from the bandage without detaching the bandage from a patient's skin. The preferred attachment device is the double-sided tape 114 shown in FIG. 30, which has been described in detail hereinabove. Another suitable attachment device is shown in FIG. 31 wherein the water heater 302 is provided with an adhesive layer 326 and a release liner 328. The release liner 328 is simply pulled from the adhesive layer 326 and the adhesive layer 326 is employed for attaching the water heater 302 to the polymeric surface 106 of the bandage 102.

Figure 32:
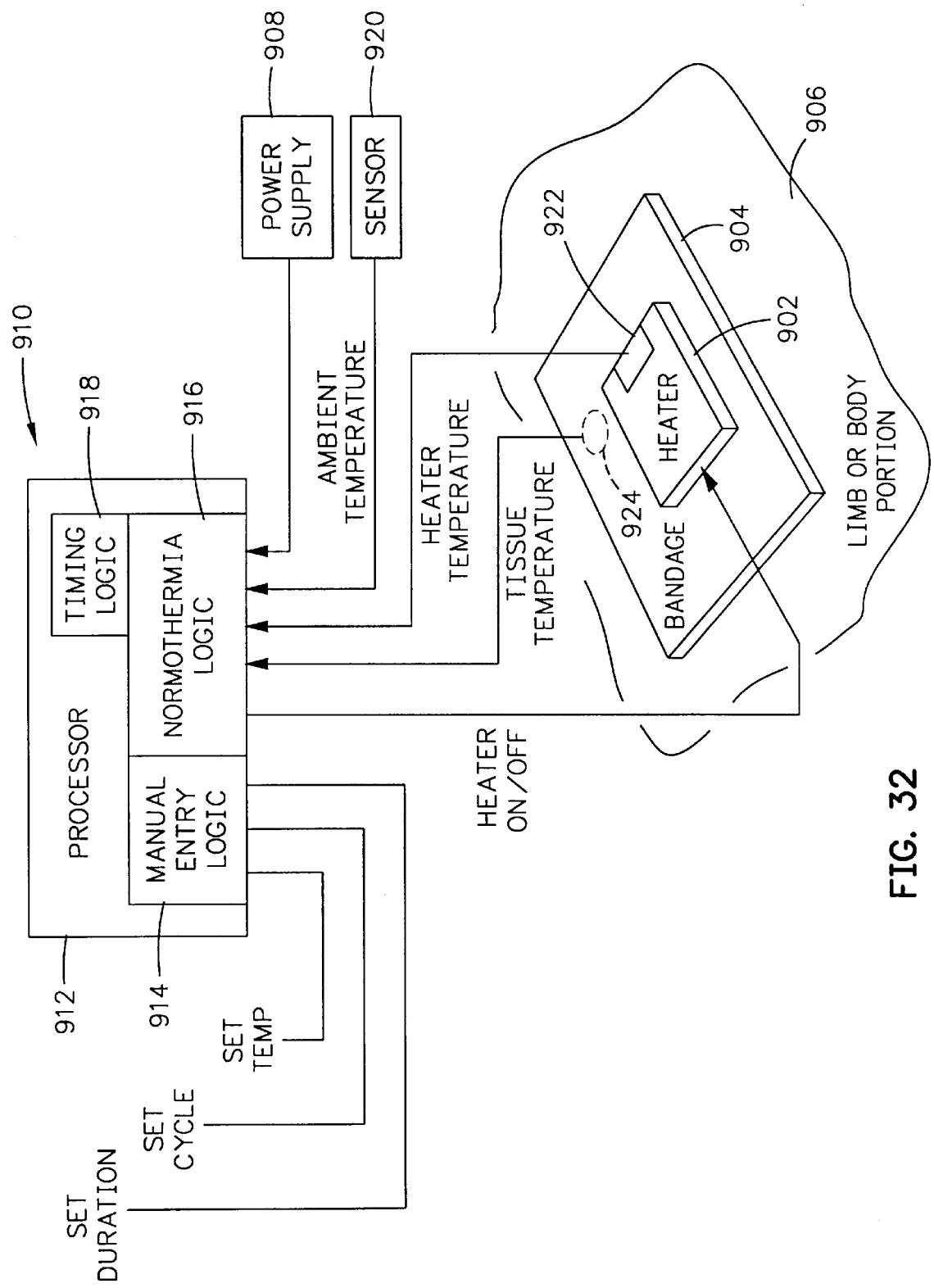
FIG. 32 is a block diagram that illustrates the present wound treatment apparatus for implementing normothermic heat therapy.

FIG. 32 is a block diagram of a wound treatment apparatus 900 for providing normothermic heat therapy to a wound on a limb or body portion of a patient. The wound treatment apparatus 900 includes a heater 902 disposed on a bandage 904 over a wound treatment area (not shown) on a limb or body portion 906 of a person or patient. The heater 902 is disposed on the bandage 904 over the treatment area for conduction of heat from the heater 902, through bandage 906, So the treatment area. The heater 902 makes contact with the bandage 904 and may be attached to it by any of the numerous attachment schemes discussed previously, or any equivalents thereto. A power supply 908 provides electrical power to the heater 902 by way of a controller 910. The controller 910 may comprise, for example, a processor 912. Preferably the processor 912 includes manual entry logic 914, normothermia logic 916, and timing logic 918. Manual entry logic 914 may be conventional logic of the kind used, for example, to set various timing functions in a wrist watch. For the purposes of the controller 910, the manual entry logic 914 receives, from conventional manually-operated devices, such as buttons, a user input for setting a temperature of the heater 902 (SET TEMP), a user input for setting a number of cycles (SET CYCLE), and a user input for setting cycle duration (SET DURATION). These inputs are only examples. Other inputs may set therapy cycle duration, number of duty cycles per therapy cycle, average heater temperature per duty cycle, average heater temperature per therapy cycle, and peak and minimum temperatures for a therapy cycle. The timing logic 918 is conventional, providing timing functions for implementing cycle times and durations. The normothermia logic 916 controls connection of the power supply 908 to the heater 902 in a manner that implements normothermic treatment of a wound by heating the tissue in and near a wound treatment area to a temperature in a normothermic range. In order to control the course of such treatment, the normothermia logic 916 receives signals from sensors 920, 922 and 924 that indicate, respectively, an ambient temperature, the heater temperature, and the tissue temperature at or near the treatment area. The heater 902 is powered by a heater on/off signal that comprises a voltage obtained from the power supply 908.

The controller 910 may comprise a programmable, general purpose processor, a programmable special purpose processor, a specially-designed electronic circuit, or an application specific integrated circuit (ASIC), or any equivalent. Preferably, the controller 910 is a multi-state machine that may transition between specified states of operation automatically, in response to manual inputs, or programmed functions, or both. Assuming that at least some of the functions of the controller 910 are implemented in the controller by programming, the normothermia logic 916 may include a control program embodied in a programmable memory, a programmable logic circuit, or both. Further the manual entry logic 914 permits a user to enter or change parameter values and provides user control of functions and operations. The controller 910, and power supply 908 may be integrated mechanically into a single unit that may include the heater 902, or provided in a separate package that is electrically connected to the heater 902. The power supply 908 may comprise a battery, battery pack, an AC/DC converter, or any other equivalent device that may be switched on and off to the heater 902.

The controller 910 controls the temperature and one or more heat cycles of the heater 902 so as to maintain normothermic or near-normothermic tissue temperature at a wound treatment area on a person's body. By sensing the temperature of tissue at the wound treatment area with the sensor 924, the temperature of the heater 902 may be controlled to accomplish this purpose. Alternatively, normothermic or near-normothermic temperature of tissue at the treatment area may be maintained in response to the temperature of the heater itself 902, which is sensed by the sensor 922. If the sensor 922 at the heater 902 is used instead of the sensor 924, compensation may be made for any heat loss in the thermal path from the heater 902, through the bandage 904, to the treatment area. Preferably, the heater 902, the bandage 904, and the interface between them are designed to minimize heat loss. If heat loss is small, any differential between heat measured by the sensor 922 and heat measured by the sensor 924 may be small enough to merit elimination of one of the sensors. In any event, either, or both, of the sensors 922 and 924 may be deployed to measure the temperature of the heater 902 and the tissue at the treatment area.

Preferably, the controller 910 operates the heater 902 in such a manner as to maintain a limited heat range, centered on the normothermic level of temperature, at a treatment area. Preferably, this range is from about 36° C. to about 38° C., although it may be somewhat greater or smaller. To accomplish this purpose, the controller 910 may turn the heater 902 on and off over one or more duty cycles of the heater 902 and one or more therapy cycles. In this regard, a therapy cycle is a plurality of duty cycles followed by a period of time during which the heater 902 is off. A plurality of therapy cycles may constitute a therapeutic sequence that may last for one day or longer. After a number of therapy cycles in a therapeutic sequence, the heater 902 is turned off for a longer period of time and then may be turned on again for another plurality of therapy cycles. When the heater 902 is turned off at the end of a therapeutic sequence, the temperature of the wound treatment apparatus 900 and the temperature of the treatment area may approach the ambient temperature in the space where the patient is located. It is assumed that the ambient temperature is at or below normothermia.

Figure 33:
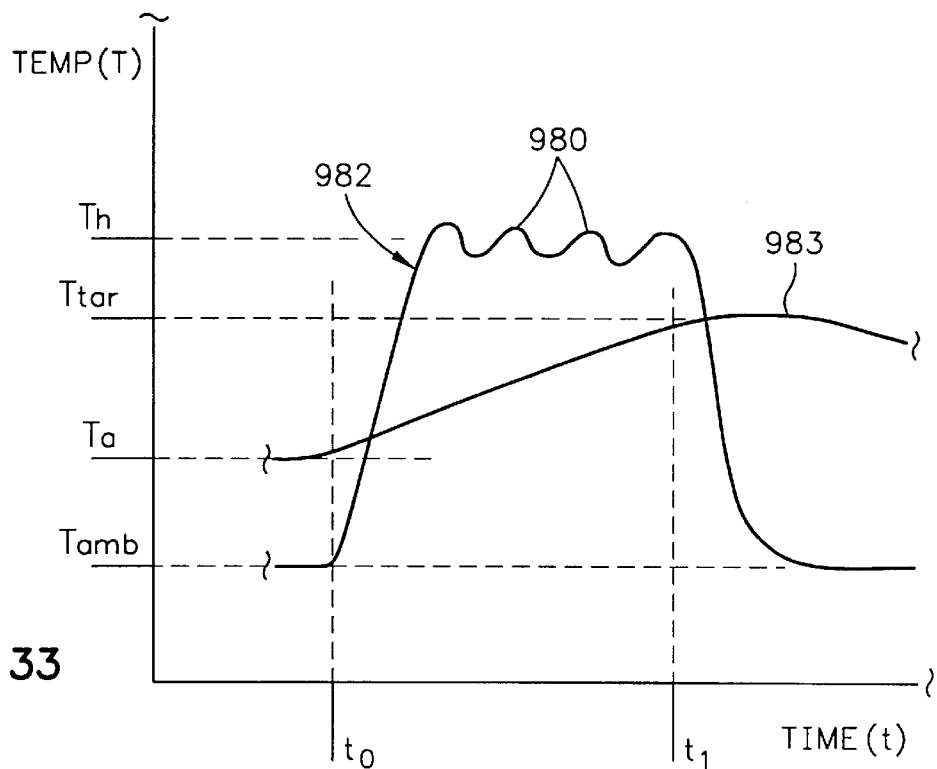
FIG. 33 is a graph showing the temperatures at the wound and the heater over a plurality of duty cycles.

By way of example, and without limiting the scope of treatment versatility, FIG. 33 is a graphic representation of a normothermic treatment regimen that may be implemented by the normothermia logic 916 and actually delivered by operation of the apparatus 900. In FIG. 33, a plurality of duty cycles 980 has been depicted as a curve 982 over a therapy cycle; tissue temperature response to the therapy cycle is represented by a curve 983, the tissue temperature response being indicated by the temperature sensor 924 of FIG. 32. Time (t) is represented along the abscissa and temperature (T) along the ordinate. A tissue temperature target value $T_{tar}$, which is preferably normothermic, has been entered into the heater controller 910 and the heater 902 is started at $t_0$. The tissue temperature is initially at $T_a$ and the heater 902 is initially at ambient temperature $T_{amb}$. By turning on the heater at $t_0$, the first of the plurality of duty cycles for the heater begins in order to provide heat with which to raise the tissue temperature to $T_{tar}$. The heater controller 910 raises the operating temperature of the heater 902 to $T_h$ based on the value, either programmed or input, for $T_{tar}$; the heater controller causes the heater 902 to operate according to a duty cycle to provide $T_{tar}$ to at least a portion of the selected wound treatment area. The tissue target temperature $T_{tar}$ value is reached at $t_1$, at which time the heater is turned off. Alternatively, although not shown, upon reaching $T_{tar}$, the controller 910 could have changed $T_h$ to a lower value and kept the heater active in order to maintain the tissue temperature at $T_{tar}$.

Figure 34:
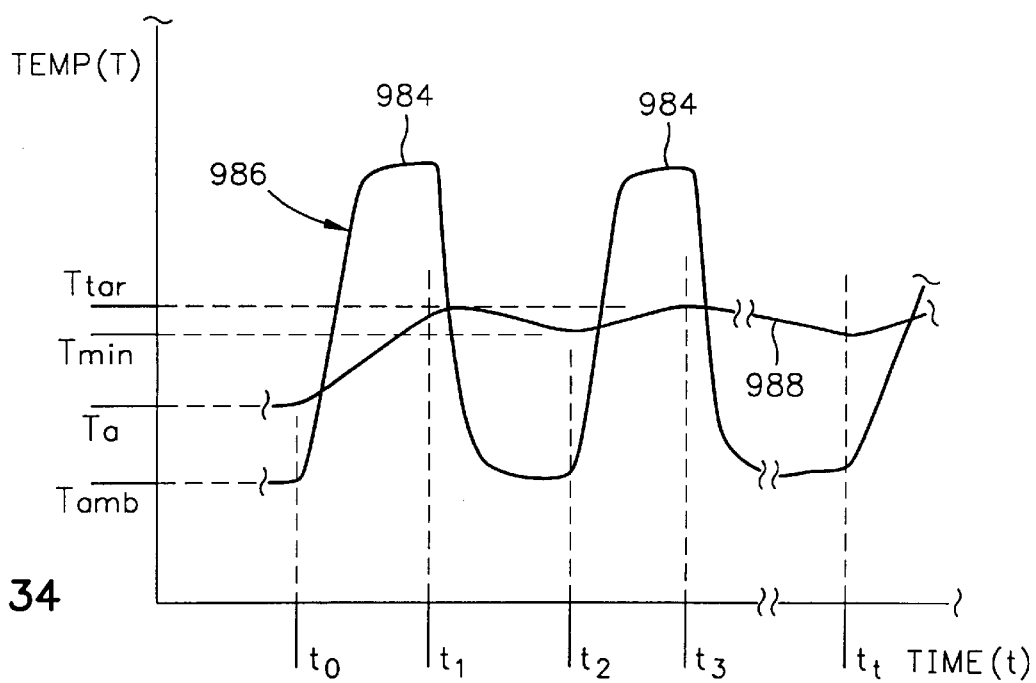
FIG. 34 is a temperature versus time graph showing the temperature at the wound and the heater over a number of therapy cycles.

By way of another example, and not limiting in scope of treatment versatility, a plurality of therapy cycles 984 actually delivered by operation of the apparatus 900 are depicted in FIG. 34, wherein individual duty cycles within each therapy cycle have been averaged out for purposes of clarification and for purposes herein are treated as the heater being "on". A first therapy cycle begins at to as depicted by the heater 902 turning "on", as shown by a heater temperature curve 986. A tissue temperature target value $T_{tar}$ has been entered into the heater controller 910; the tissue temperature response is shown in a curve 988. The tissue start temperature is $T_a$ and the starting heater temperature is at about ambient, $T_{amb}$. The heater remains "on" until the tissue temperature has reached $T_{tar}$ as monitored directly by the sensor 924 in FIG. 32, or as predicted by an appropriate heating paradigm employing the sensor 922. As shown, $T_{tar}$ is reached at $t_1$ at which time the heater is turned "off". As in the previous example, an alternative is that the heater controller 910 selects an alternate heating output, chosen to maintain the tissue temperature at about $T_{tar}$. As depicted in FIG. 34, however, the tissue temperature is allowed to drift downwardly with the heater "off" until the tissue temperature reaches a temperature $T_{min}$ that is either programmed or pre-selected as a value in the controller 910 or the program control 912. Upon reaching $T_{min}$, the heater 902 is turned "on" again, as shown at $t_2$, so as to provide heat to the selected treatment area so as to raise the tissue temperature to $T_{tar}$. This first therapy cycle ends at $t_2$ when a second therapy cycle begins by turning "on" the heater again. As in the first therapy cycle, this second therapy cycle provides heat to the tissue to reach the tissue target temperature, $T_{tar}$. Alternatively this second therapy cycle may have a different $T_{tar}$, or optionally may have a different cycle length calling for the controller 910 to change the heater output. The present invention anticipates the use of any number of therapy cycles having any length or duration per cycle and different set temperatures, and a plurality of therapy cycles contributing to a therapeutic sequence.

For the above examples, $T_{tar}$ may be programmed in the controller 910 or directly selected by an operator employing the manual entry logic 914. For the present invention, this tissue target temperature is in a range preferably of about 36° C. to 38° C. Another aspect of therapy control according to the present invention is the averaging tissue target temperatures of duty cycles, therapy cycles and a therapeutic sequence, as depicted in FIG. 35.

Figure 35:
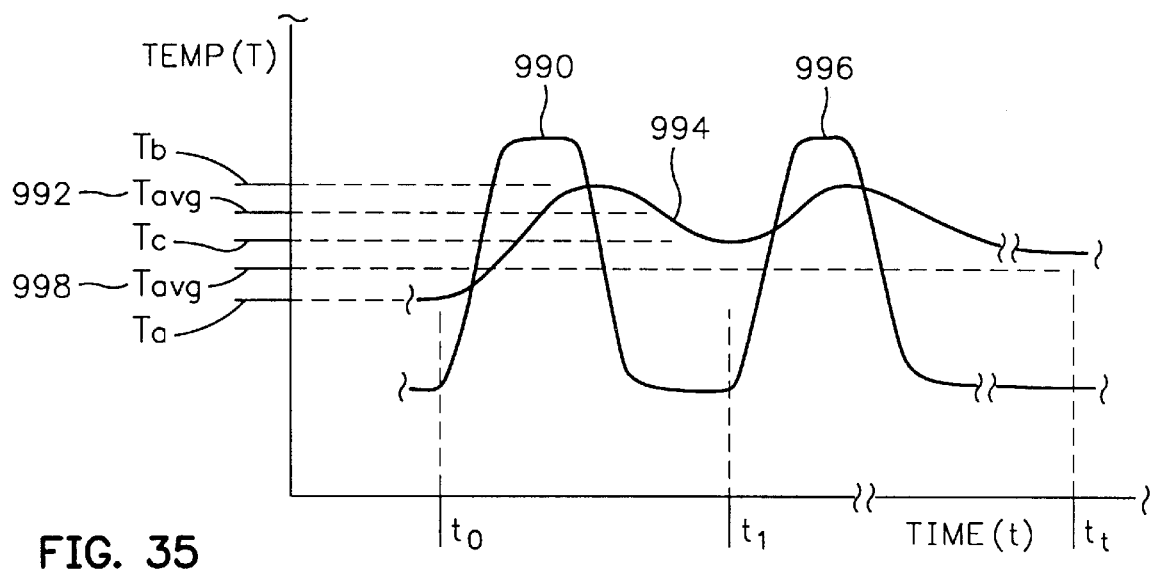
FIG. 35 is a graph showing temperature versus time similar to the graph shown in FIG. 38 except the temperature is set at an average instead of a set amount.

In FIG. 35, a therapy cycle 990 starts at $t_0$ and ends at $t_1$. The tissue target temperature average $T_{avg}$ 992 for this therapy cycle may be selected or programmed. The tissue temperature change, as depicted by a temperature curve 994, begins at a temperature $T_a$, rises as it is heated by the heater to a peak temperature $T_b$ during the "on" phase of the heater 902, as depicted by a heater temperature curve, and then drifts downwardly to a minimum temperature $T_c$ over an additional period of time such that the total period of time is equivalent to the period $t_0$ to $t_1$. $T_{avg}$ 992 represents the average of the temperatures between $T_c$ and $T_b$, wherein each of the temperature $T_a$ and $T_c$ are within the normothermic range of 3620 C. to 38° C.

An alternative approach, also depicted in FIG. 35, anticipates the programming of a number of therapy cycles as elements of a therapeutic sequence, in this example there being two therapy cycles 990 and 996 of varying times and tissue target temperatures. The present invention provides for the inputting of an average tissue target temperature $T_{avg}$ 998 between minimum and peak temperatures $T_a$ and $T_c$ for a therapeutic sequence extending from $t_0$ to $t_t$. A tissue temperature response curve has not been shown for this example.

Figure 36:
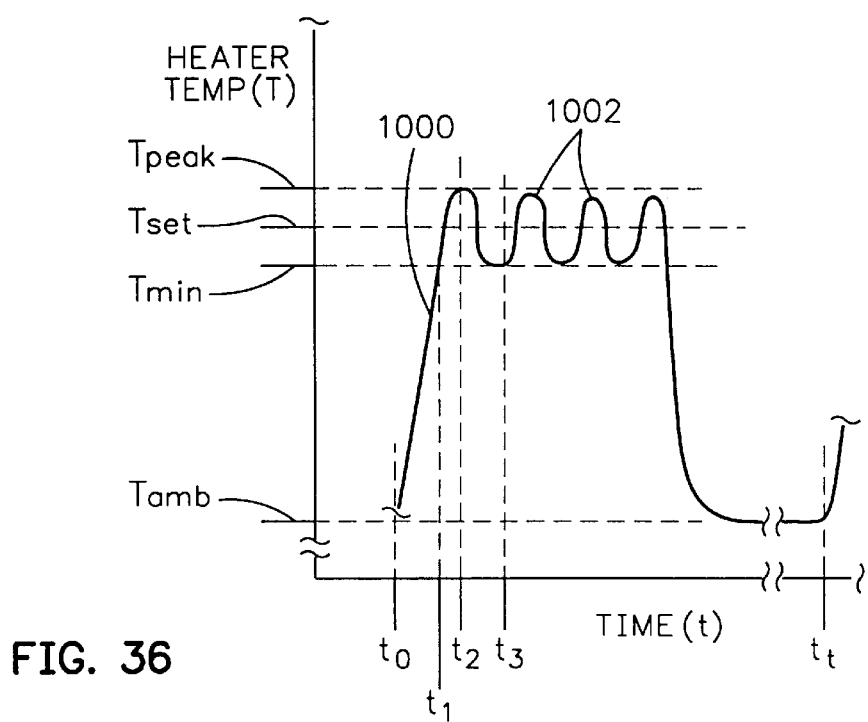
FIG. 36 is a graph of temperature versus time for a plurality of duty cycles wherein the temperature is sensed at the heater.

By way of example, and not limiting in scope of treatment versatility, FIG. 36 is a graphic representation of a therapy cycle 1000 represented by a plurality of duty cycles 1002. At $t_0$, the heater is at ambient temperature $T_{amb}$ and the first of the duty cycles 1002 begins at $t_0$ when the heater 902 reaches $T_{min}$. Upon reaching $T_{peak}$ by $t_1$, the heater power is turned off and the heater cools to $T_{min}$. The first duty cycle is completed at $t_3$ when the heater is turned back on to begin the next duty cycle. This first duty cycle and subsequent duty cycles maintain an average heater temperature $T_{set}$ as sensed by the temperature sensor 922 in FIG. 32. The duty cycle can also be governed by the total duration $t_1$ to $t_3$ and the ratio of heat on duration $t_1$ to $t_3$ over total duration $t_1$ to $t_3$. A therapy cycle for this example is the time duration from $t_0$ $t_t$ during which time the heater temperature has been allowed to fall to $T_{amb}$, where at $t_t$ the heating regimen begins again starting the next therapy cycle. As shown in FIG. 39, a peak temperature, $T_{peak}$ and a minimum temperature $T_{min}$ may be parameters inputted into the program. An average temperature $T_{set}$ may then be selected to operate between $T_{min}$ and $T_{peak}$ within a normothermic range 36° C. to 38° C.

Figure 37:
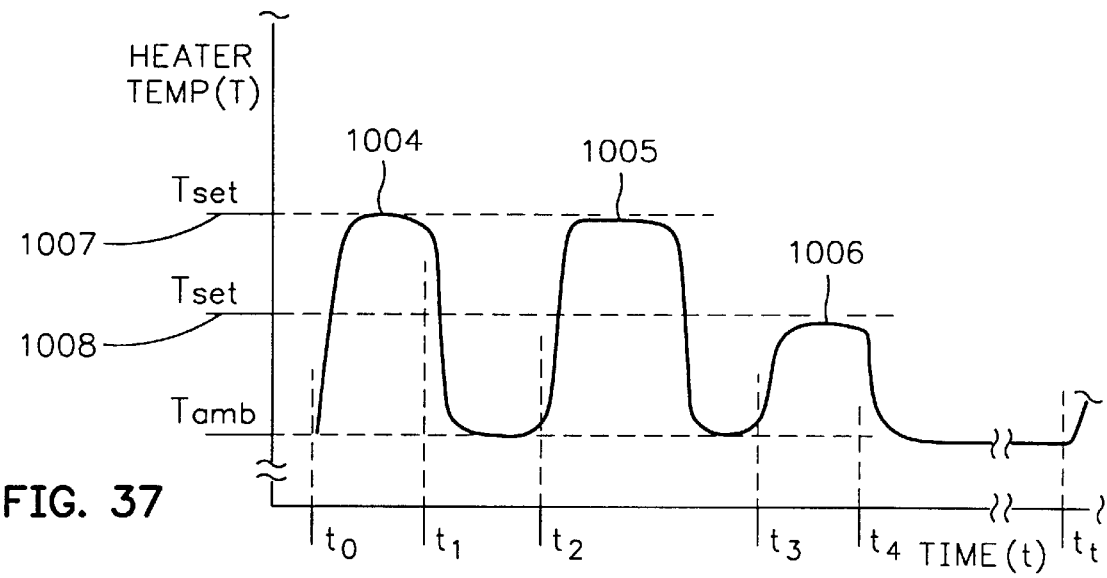
FIG. 37 is a graph of temperature versus time of a plurality of therapy cycles wherein the temperature is sensed at the heater.

By way of another example, and not limiting in scope of treatment versatility, a plurality of therapy cycles 1004, 1005 and 1006 are depicted in FIG. 37, wherein individual duty cycles within each therapy cycle have been averaged out for purposes of clarification and for purposes herein are treated as the heater being "on". A first therapy cycle begins at to as depicted by the heater turning "on", i.e., a series of duty cycles is begun, and the heater heats to $T_{set}$ 1007. This "on" segment goes until $t_1$ at which time the heater is turned "off" and allowed to cool to $T_{amb}$. This first therapy cycle 1004 ends at $t_2$ when the second therapy cycle 1005 begins by turning "on" the heater 902 again. As in the first therapy cycle, this second therapy cycle heats to $T_{set}$ 1009 and has a duration from $t_2$ to $t_3$. The third therapy cycle 1006 begins at $t_3$ turning "on" the heater 902. For purposes of example to depict anticipated versatility of the present invention, this third therapy cycle is given a different $T_{set}$ 1008. The heater 902 is turned "off" at $t_4$. This entire period of multiple therapy cycles may also be part of a therapeutic sequence as that period of time from $t_0$ to $t_f$ encompassing three therapy cycles. The present invention anticipates the use of any number of therapy cycles having any length or duration per cycle and different set temperatures, whether the temperatures be a set level or averaged.

Figure 38:
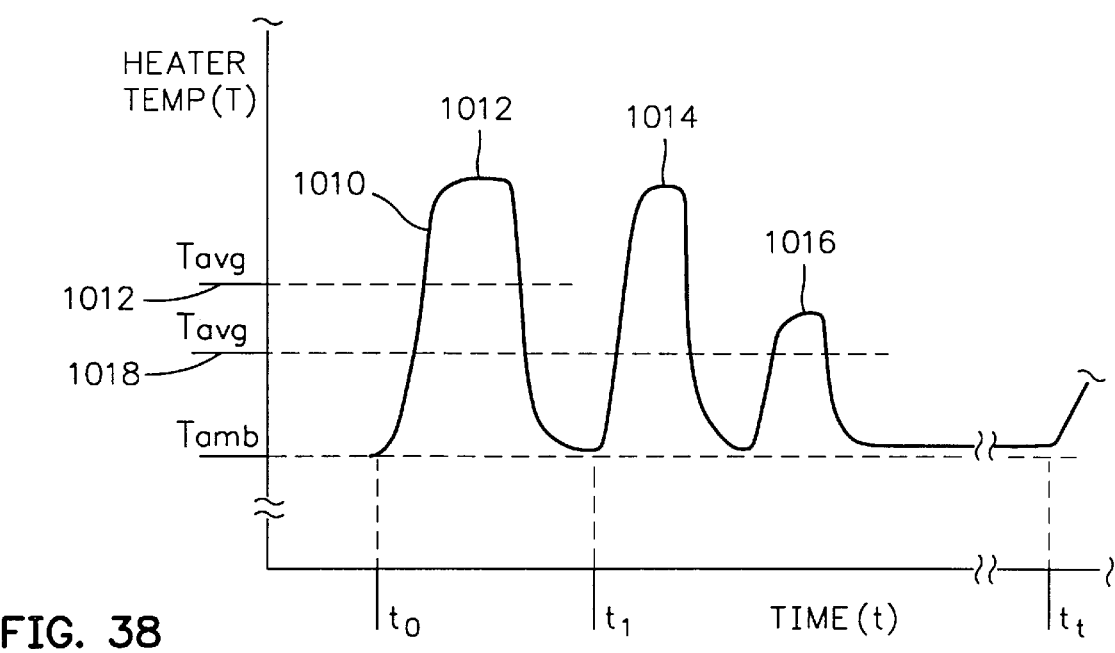
FIG. 38 is a graph of temperature versus time showing a plurality of therapy cycles wherein temperature is sensed at the heater.

Another aspect of heat therapy control is the averaging of a number of therapy cycles in a therapeutic sequence, as depicted in FIG. 38. In FIG. 38 a therapy cycle 1010 starts at $t_0$ and ends at $t_1$. The overall average heater temperature $T_{avg}$ for this therapy cycle may be selected or programmed. The heater 902, beginning at an ambient temperature $T_{amb}$, heats to an appropriate temperature for the "on" phase and then is "off" for an additional appropriate time such that the total period of time is equivalent to the period $t_0$ to $t_1$ and the average temperature for this period is equivalent to $T_{avg}$ 1012.

An alternative approach, also depicted in FIG. 38, anticipates the selection or programming of a number of therapy cycles as elements of a therapeutic sequence, in this example there being three therapy cycles 1012, 1014 and 1016 of varying time and heater temperatures. The present invention versatility provides for the inputting of an average temperature $T_{avg}$ 1018 for the therapeutic sequence. The therapeutic sequence begins at time $t_0$ and ends at time $t_f$. The heater temperatures and durations of the therapy cycles within the therapeutic sequence are averaged by the controller 910 over the entire period of time from $t_0$ to $t_f$ so as to achieve the therapeutic average temperature $T_{avg}$ 1018. Each of these average temperatures is preferably at a level to maintain an average tissue temperature of between 36° C. to 38° C. for implementing normothermic heat treatment during a series of duty cycles followed by a heater off period at the end of each therapy cycle. It should be understood, however, that the invention can be employed to maintain tissue temperature at any desired set temperature level or temperature average.

Clearly, other embodiments and modifications of this invention will occur readily to those of ordinary skill in the art in view of these teachings. Therefore, this invention is to be limited only by the following claims, which include all such embodiments and modifications when viewed in conjunction with the above specification and accompanying drawings.

We claim:

1. A wound treatment apparatus comprising:
    a bandage having first and second surfaces, the first surface of the bandage corresponding to a wound treatment area;
    a heater;
    the heater being disposed against the second surface of the bandage; and,
    a controller connected to the heater for maintaining a temperature at a wound treatment area in a normothermic range.

2. The wound treatment apparatus as claimed in claim 1 wherein the bandage is thermally conductive.

3. The wound treatment apparatus as claimed in claim 2, the bandage including material selected from the group consisting of hydrogel, hydrocolloid, hydrated alginate, hydrated gauze, hydrate polymeric foam and polymeric film.

4. The wound treatment apparatus as claimed in claim 1, wherein the heater includes an electrically resistive filament.

5. The wound treatment apparatus as claimed in claim 1, the heater including a warm water pad.

6. The wound treatment apparatus as claimed in claim 1, wherein the heater includes a flexible planar member and means disposed in the flexible planar member for generating heat substantially uniformly distributed within the flexible planar member.

7. The wound treatment apparatus as claimed in claim 1, wherein the heater includes a flexible planar member and means disposed within the flexible planar member for heating a portion of the flexible planar member.

8. The wound treatment apparatus as claimed in claim 1, further including an attachment means for retaining the heater over the second surface of the bandage.

9. The wound treatment apparatus as claimed in claim 8, wherein the heater includes a first surface and the attachment means is for holding the first surface of the heater in at least partial contact with the second surface of the bandage.

10. The wound treatment apparatus as claimed in claim 1, the controller including means for cycling the operation of the heater on and off.

11. The wound treatment apparatus as claimed in claim 10, wherein the controller includes programmable means for cycling the operation of the heater over a duty cycle.

12. The wound treatment apparatus as claimed in claim 10, wherein the controller includes programmable means for cycling the operation of the heater over a therapy cycle.

13. The wound treatment apparatus as claimed in claim 12, wherein the therapy cycle includes a plurality of duty cycles.

14. The wound treatment apparatus as claimed in claim 10, wherein the controller includes programmable means for controlling the operation of the heater over a therapeutic sequence, the therapeutic sequence including one or more therapy cycles, each therapy cycle including one or more duty cycles.

15. The wound treatment apparatus as claimed in claim 1, wherein the controller includes selectable average temperature values, each indicating an average temperature of the heater.

16. The wound treatment apparatus as claimed in claim 1, the controller including means for causing the heater to operate at an average temperature over a duty cycle.

17. The wound treatment apparatus as claimed in claim 1, the controller including means for causing the heater to operate at an average temperature over a therapy cycle.

18. The wound treatment apparatus as claimed in claim 1, the controller including means for causing the heater to operate at an average temperature over a therapeutic sequence.

19. The wound treatment apparatus as claimed in claim 18, the therapeutic sequence including a plurality of therapy cycles.

20. The wound treatment apparatus as claimed in claim 19, each therapy cycle including a plurality of duty cycles.

* * * * *